(12) United States Patent
Lo et al.

(10) Patent No.: US 10,240,199 B2
(45) Date of Patent: Mar. 26, 2019

(54) MATERNAL PLASMA TRANSCRIPTOME ANALYSIS BY MASSIVELY PARALLEL RNA SEQUENCING

(71) Applicant: The Chinese University of Hong Kong, Shatin, New Territories (CN)

(72) Inventors: Yuk-Ming Dennis Lo, Kowloon (CN); Rossa Wai Kwun Chiu, Shatin (CN); Kwan Chee Chan, Kowloon (CN); Peiyong Jiang, Shatin (CN); Bo Yin Tsui, Ma On Shan (CN)

(73) Assignee: The Chinese University of Hong Kong, New Territories (HK)

( * ) Notice: Subject to any disclaimer, the term of this patent is extended or adjusted under 35 U.S.C. 154(b) by 1050 days.

(21) Appl. No.: 14/194,294

(22) Filed: Feb. 28, 2014

(65) Prior Publication Data

US 2014/0243212 A1   Aug. 28, 2014

Related U.S. Application Data

(60) Provisional application No. 61/770,985, filed on Feb. 28, 2013.

(51) Int. Cl.
*G06F 19/00* (2018.01)
*C12Q 1/6883* (2018.01)
*G06F 19/22* (2011.01)

(52) U.S. Cl.
CPC ........... *C12Q 1/6883* (2013.01); *G06F 19/22* (2013.01); *C12Q 2600/156* (2013.01)

(58) Field of Classification Search
CPC ............ C12Q 2537/165; C12Q 1/6809; C12Q 2537/16; C12Q 1/6883; C12Q 1/6869; C12Q 1/6827; C12Q 2600/156; C12Q 1/6858; C12Q 1/68; C12Q 2535/122; C12Q 2600/158; G06F 19/22; G06F 19/18; G06F 19/00; G06F 19/24; G06F 19/12; G06F 19/20; G06F 19/34; G06F 19/16;

(Continued)

(56) References Cited

U.S. PATENT DOCUMENTS

2002/0045176 A1   4/2002   Lo et al.
2009/0087847 A1   4/2009   Lo et al.

(Continued)

FOREIGN PATENT DOCUMENTS

CN   102758014 A   10/2012
CN   102770558 A   11/2012

(Continued)

OTHER PUBLICATIONS

Written Opinion dated May 1, 2016 in SG Patent Application No. 11201506516T. 12 pages.

(Continued)

*Primary Examiner* — Mary K Zeman
(74) *Attorney, Agent, or Firm* — Kilpatrick Townsend & Stockton LLP

(57) ABSTRACT

Methods are provided for diagnosing pregnancy-associated disorders, determining allelic ratios, determining maternal or fetal contributions to circulating transcripts, and/or identifying maternal or fetal markers using a sample from a pregnant female subject. Also provided is use of a gene for diagnosing a pregnancy-associated disorder in a pregnant female subject.

20 Claims, 29 Drawing Sheets

(58) Field of Classification Search
CPC ...... G06F 19/3431; G06F 17/10; G06F 17/11; G06F 19/14; G06F 19/26; G16H 50/20; G16H 10/40; G06N 7/005; G06N 99/005
See application file for complete search history.

(56) References Cited

U.S. PATENT DOCUMENTS

| | | | |
|---|---|---|---|
| 2010/0311046 | A1 | 12/2010 | Lo et al. |
| 2011/0201507 | A1 | 8/2011 | Rava et al. |
| 2012/0184449 | A1* | 7/2012 | Hixson ............ G06F 19/22 506/7 |
| 2013/0029852 | A1 | 1/2013 | Rava et al. |
| 2016/0206474 | A1 | 7/2016 | Hanft et al. |

FOREIGN PATENT DOCUMENTS

| | | |
|---|---|---|
| EP | 1859051 | 11/2007 |
| EP | 1859051 A | 8/2009 |
| JP | 2008524993 A | 7/2008 |
| TW | 201243326 A1 | 11/2012 |
| WO | 2004/065629 A1 | 8/2004 |
| WO | 2005/021793 A1 | 10/2005 |
| WO | 2006097051 A1 | 9/2006 |
| WO | 2009/100029 A1 | 8/2009 |
| WO | 2012/058316 A1 | 5/2012 |
| WO | 2012/088348 A2 | 6/2012 |
| WO | 2012/093331 A1 | 7/2012 |
| WO | 2013/041921 A1 | 3/2013 |

OTHER PUBLICATIONS

Extended European Search Report dated Oct. 14, 2016 in EP Patent Application No. 14757525.2. 19 pages.
Lo, Y. M. Dennis et al.; "Digital PCR for the molecular detection of fetal chromosomal aneuploidy"; PNAS; Aug. 7, 2007; vol. 104, No. 32; pp. 13116-13121.
Purwosunu, Yuditiya et al.; "Cell-free mRNA concentrations of CRH, PLAC1, and selectin-P are increased in the plasma of pregnant women with preeclampsia"; Prenatal Diagnosis; 2007; vol. 27, No. 8; pp. 772-777.
Go, Attie T.J.I. et al.; "Non-invasive aneuploidy detection using free fetal DNA and RNA in maternal plasma: recent progress and future possibilities"; Human Reproductive Update; 2011; vol. 17, No. 3; pp. 372-382.
Oudejans, Cees B.M., "Maternal plasma RNA sequencing"; Clinical Biochemistry; 2015; 48; pp. 942-947.
International Search Report from PCT/IB2014/059351, dated Jun. 30, 2014.
Anders et al.; "Detecting differential usage of exons from RNA-seq data"; Genome Res.; 22:2008-2017 (2012) ePub Jun. 21, 2012.
Cabili et al.; "Integrative annotation of human large intergenic noncoding RNAs reveals global properties and specific subclasses"; Genes Dev.; 25:1915-1927 (2011) ePub Sep. 2, 2011.
Chim et al.; "Detection and Characterization of Placental MicroRNAs in Maternal Plasma"; Clin. Chem.; 54(3):482-490 (2008).
Chim et al.; "Systematic Identification of Spontaneous Preterm Birth-Associated RNA Transcripts in Maternal Plasma"; PLoS One 7(4): e34328 (2012) doi:10.1371/journal.pone.0034328 ePub Apr. 5, 2012.
Daelemans et al.; "High-throughput analysis of candidate imprinted genes and allele-specific gene expression in the human term placenta"; BMC Genetics, 11:25 (2010).
Farina et al.; "Fetal DNA in maternal plasma as a screening variable for preeclampsia. A preliminary nonparametric analysis of detection rate in low-risk nonsymptomatic patients"; Prenat. Diagn.; 24:83-86 (2004).
Fleischhacker and Schmidt; "Circulating nucleic acids (CNAs) and cancer—A survey"; Biochimica et Biophysica Acta; 1775:181-232 (2007).

Frost et al.; "Evaluation of Allelic Expression of Imprinted Genes in Adult Human Blood"; PLoS One; 5(10):e13556 (Oct. 21, 2010). doi:10.1371/journal.pone.0013556.
Go et al.; "Detection of Placental Transcription Factor mRNA in Maternal Plasma"; Clin. Chem.; 50(8):1413-1414 (2004).
Kim et al.; "Transcriptome landscape of the human placenta"; BMC Genomics; 13:115 (2012).
Li et al.; "A comprehensive survey of maternal plasma miRNAs expression profiles using high-throughput sequencing"; Clinica Chimica Acta; 413:568-576 (2012).
Lo et al.; "Maternal Plasma DNA Sequencing Reveals the Genome-Wide Genetic and Mutational Profile of the Fetus"; Sci. Transl. Med.; 2(61):61ra91 (Dec. 8, 2010); DOI: 10.1126/scitranslmed.3001720.
Lo et al.; "Plasma placental RNA allelic ratio permits noninvasive prenatal chromosomal aneuploidy detection"; Nat. Med.; 13(2):218-223 (2007) ePub Jan. 7, 2007.
Lun et al.; "Noninvasive Prenatal Methylomic Analysis by Genomewide Bisulfite Sequencing of Maternal Plasma DNA"; Clin. Chem.; 59(11):1583-1594 (2013).
Miura et al.; "The possibility of microarray-based analysis using cell-free placental mRNA in maternal plasma"; Prenat. Diagn.; 30:849-861 (2010).
Mortazavi et al.; "Mapping and quantifying mammalian transcriptomes by RNA-Seq"; Nat. Meth.; 5(7):621-628 (2008) ePub May 30, 2008.
Ng et al.; "Evaluation of Human Chorionic Gonadotropin—Subunit mRNA Concentrations in Maternal Serum in Aneuploid Pregnancies: A Feasibility Study"; Clin. Chem.; 50(6):1055-1057 (2004).
Ng et al.; "mRNA of placental origin is readily detectable in maternal plasma"; Proc. Natl. Acad. Sci. USA; 100(8):4748-4753 (2003).
Ng et al.; "The Concentration of Circulating Corticotropin-releasing Hormone mRNA in Maternal Plasma Is Increased in Preeclampsia"; Clin. Chem.; 49(5):727-731 (2003).
Pang et al.; "A strategy for identifying circulating placental RNA markers for fetal growth assessment"; Prenat. Diagn.; 29:495-504 (2009) ePub Feb. 18, 2009.
Pickrell et al.; "Understanding mechanisms underlying human gene expression variation with RNA sequencing"; Nature; 464(7289):768-772 (2010). doi:10.1038/nature08872 (NIH-PA Author Manuscript).
Poon et al.; "Presence of Fetal RNA in Maternal Plasma"; Clin. Chem.; 46(1):1832-1834 (2000).
Purwosunu et al.; "Cell-Free mRNA Concentrations of Plasminogen Activator Inhibitor-1 and Tissue-Type Plasminogen Activator Are Increased in the Plasma of Pregnant Women with Preeclampsia"; Clin. Chem.; 53(3):399-404 (2007).
Smets et al.; "Novel biomarkers in preeclampsia"; Clinica Chimica Acta; 364:22-32 (2006).
Smith et al.; "Whole transcriptome RNA-Seq allelic expression in human brain"; BMC Genomics; 14:571 (2013).
St Laurent et al.; "Intronic RNAs constitute the major fraction of the non-coding RNA in mammalian cells"; BMC Genomics; 13:504 (2012).
Sultan et al.; "A Global View of Gene Activity and Alternative Splicing by Deep Sequencing of the Human Transcriptome"; Science; 321:956-960 (2008).
Tsui et al.; "Non-invasive prenatal detection of fetal trisomy 18 by RNA—SNP allelic ratio analysis using maternal plasma SERPINB2 mRNA: a feasibility study". Prenat. Diagn.; 29:1031-1037 (2009) ePub Jul. 31, 2009.
Tsui et al.; "Synergy of Total PLAC4 RNA Concentration and Measurement of the RNA Single-Nucleotide Polymorphism Allelic Ratio for the Noninvasive Prenatal Detection of Trisomy 21"; Clin. Chem.; 56(1):73-81 (2010).
Tsui et al.; "Systematic micro-array based identification of placental mRNA in maternal plasma: towards non-invasive prenatal gene expression profiling". J. Med. Genet.; 41:461-467 (2004).
Wang et al.; "The Complex Exogenous RNA Spectra in Human Plasma: An Interface with Human Gut Biota?" PLoS One; 7(12): e51009 (2012). doi:10.1371/journal.pone.0051009.

(56) References Cited

OTHER PUBLICATIONS

Williams et al.; "Comprehensive profiling of circulating microRNA via small RNA sequencing of cDNA libraries reveals biomarker potential and limitations". *Proc. Natl. Acad. Sci. USA*; 110(11):4255-4260 (2013).
Wong et al.; "Circulating Placental RNA in Maternal Plasma Is Associated with a Preponderance of 5 mRNA Fragments: Implications for Noninvasive Prenatal Diagnosis and Monitoring"; *Clin. Chem.*; 51(10):1786-1795 (2005).
Wu et al.; "BioGPS: an extensible and customizable portal for querying and organizing gene annotation resources"; Genome Biology; 10:R130 (Nov. 17, 2009) (doi:10.1186/gb-2009-10-11-r130).
English translation of Office Action dated Mar. 7, 2017 in JP Patent Application No. 2015-559600. 9 pages.
Heung, Macy M.S. et al.; "Placenta-Derived Fetal Specific mRNA Is More Readily Detectable in Maternal Plasma than in Whole Blood"; PLoS ONE; Jun. 10, 2009; vol. 4, Issue 6; e5858; 11 pages.
Liao, Gary J.W. et al.; "Noninvasive Prenatal Diagnosis of Fetal Trisomy 21 by Allelic Ratio Analysis Using Targeted Massively Parallel Sequencing of Maternal Plasma DNA"; PLoS One; May 2012; vol. 7, Issue 5; e38154; 7 pages.
Enders, K.O. Ng et al.; "The Concentration of Circulating Corticotropin-releasing Hormone mRNA in Maternal Plasma Is Increased in Preeclampsia"; Clinical Chemistry; 2003; vol. 49, Issue 5; pp. 727-731.

\* cited by examiner

| Sample type | Sample | Raw reads | Preprocessed[a] reads | (%)[b] | Mappable reads[c] | (%)[d] |
|---|---|---|---|---|---|---|
| Non-pregnant female plasma | CTR081 | 180,080,810 | 23,012,332 | 12.78% | 7,708,011 | 33.50% |
| | CTR082 | 132,567,446 | 20,559,146 | 15.51% | 6,848,249 | 33.31% |
| Pre-delivery maternal plasma | M9600P | 367,301,939 | 45,255,199 | 12.32% | 16,849,461 | 37.23% |
| | M9549P | 597,724,438 | 151,243,195 | 25.30% | 34,627,313 | 22.90% |
| | M9356P | 820,742,404 | 190,030,278 | 23.15% | 14,091,631 | 7.42% |
| | M9415P | 970,145,241 | 143,615,377 | 14.80% | 41,517,504 | 28.91% |
| Post-delivery maternal plasma | M9356BP | 587,698,232 | 132,012,632 | 22.46% | 7,828,124 | 5.93% |
| | M9415BP | 853,401,365 | 101,070,496 | 11.84% | 26,707,674 | 26.42% |
| Placenta | N9356 | 202,711,386 | 169,500,629 | 83.62% | 160,417,620 | 94.64% |
| | N9415 | 257,219,381 | 203,094,642 | 78.96% | 193,126,555 | 95.09% |
| Maternal blood cells | M9600W | 163,832,386 | 38,707,658 | 23.63% | 11,348,398 | 29.32% |
| | M9549W | 240,383,043 | 83,922,150 | 34.91% | 73,117,147 | 87.12% |
| | M9356W | 208,400,902 | 60,851,642 | 29.20% | 54,974,158 | 90.34% |
| | M9415W | 265,636,207 | 49,943,628 | 18.80% | 42,670,781 | 85.44% | a. Retained reads after removal of highly repetitive reads.
b. % of the raw reads.
c. See Supplemental Data Table 2B for detailed breakdown.
d. % of the preprocessed reads.

*FIG. 4*

| Sample type | Sample | Filtered reads[a] | Analyzable reads[b] | Exon (%) | Intron (%) | Intergenic region (%)[c] |
|---|---|---|---|---|---|---|
| Non-pregnant female plasma | CTR081 | 4,186,990 | 3,521,021 | 64.00% | 6.47% | 29.53% |
|  | CTR082 | 3,594,966 | 3,253,283 | 61.93% | 7.29% | 30.78% |
| Pre-delivery maternal plasma | M9600P | 7,711,430 | 9,138,031 | 64.42% | 6.47% | 29.10% |
|  | M9549P | 20,481,388 | 14,145,925 | 41.84% | 13.16% | 45.00% |
|  | M9356P | 1,683,896 | 12,407,735 | 56.80% | 30.76% | 12.45% |
|  | M9415P | 23,164,778 | 18,352,726 | 53.61% | 10.80% | 35.59% |
| Post-delivery maternal plasma | M9356BP | 988,066 | 6,840,058 | 50.41% | 38.15% | 11.44% |
|  | M9415BP | 15,853,377 | 10,854,297 | 50.12% | 13.68% | 36.19% |
| Placenta | N9356 | 3,204,907 | 157,212,713 | 31.18% | 55.89% | 12.93% |
|  | N9415 | 4,186,711 | 188,939,844 | 26.51% | 59.59% | 13.90% |
| Maternal blood cells | M9600W | 854,869 | 10,493,529 | 69.71% | 23.50% | 6.79% |
|  | M9549W | 8,120,655 | 64,996,492 | 66.98% | 26.67% | 6.36% |
|  | M9356W | 4,255,081 | 50,719,077 | 69.13% | 24.70% | 6.16% |
|  | M9415W | 5,318,314 | 37,352,467 | 85.68% | 10.74% | 3.58% | a. Filtered reads are mostly the nuclear and mitochondrial rRNAs and tRNAs.
b. Analyzable reads = total mappable reads – filtered reads.
c. % of reads that aligned to regions outside exons and introns of the reference genes.

FIG. 5

| Fetal-specific SNP alleles (Maternal: AA, Fetal: AB) | SNPs | Fetal allele/shared allele ratio | Average RNA-SNP ratio per gene | Placenta FPKM | Blood cell FPKM | Fold-difference (Placenta/Blood cell) | Plasma FPKM |
|---|---|---|---|---|---|---|---|
| AFF1 | SNP 7:rs342462 | 0.28 | 0.52 | 149.731 | 16.1598 | 9.27 | 16.7037 |
|  | SNP 8:rs342459 | 1 |  |  |  |  |  |
|  | SNP 9:rs100299915 | 0.29 |  |  |  |  |  |
| SH3BGRL2 | SNP 13:rs1507 | 0.07 | 0.07 | 24.7477 | 40.3078 | 0.61 | 128.2908 |
| SLC38A1 | SNP 3:rs3742058 | 0.17 | 0.58 | 142.8723 | 15.1123 | 9.45 | 9.0209 |
|  | SNP 4:rs3742059 | 1 |  |  |  |  |  |
| PTTG1IP | SNP 6:rs873317 | 0.4 | 0.4 | 152.8104 | 56.4153 | 2.71 | 37.1191 |
| GIMAP1-GIMAP5 | SNP 14:rs1046355 | 0.04 | 0.04 | 15.9771 | 39.9271 | 0.4 | 77.4282 |
| CTSS | SNP 1:rs3754212 | 0.01 | 0.01 | 11.0084 | 382.8589 | 0.03 | 79.3012 |
| RHOBTB3 | SNP 10:rs34896 | 1 | 0.8 | 338.5763 | 21.5841 | 15.69 | 15.4046 |
|  | SNP 11:rs34898 | 0.6 |  |  |  |  |  |
|  | SNP 12:rs34899 | 0.8 |  |  |  |  |  |
| ARHGEF12 | SNP 2:rs192719576 | 0.09 | 0.09 | 88.5256 | 110.1833 | 0.8 | 63.7037 |
| TXNRD1 | SNP 5:rs111111979 | 0.2 | 0.2 | 65.9309 | 35.795 | 1.84 | 23.6787 |
| HPCAL1 | SNP 11:rs2270302 | 0.06 | 0.06 | 17.2498 | 42.5469 | 0.41 | 25.2768 |
| RAB4A | SNP 2:rs15452 | 0.08 | 0.08 | 12.7741 | 22.2066 | 0.58 | 72.2382 |
| PGM2 | SNP 13:rs37526683 | 0.22 | 0.22 | 33.0576 | 23.045 | 1.43 | 13.4293 |
| PSMB3 | SNP 10:rs228274 | 0.05 | 0.05 | 65.0683 | 117.5188 | 0.55 | 127.3262 |
| ADIPOR2 | SNP 4:rs12342 | 0.08 | 0.08 | 18.1942 | 18.7699 | 0.97 | 16.5717 |
|  | SNP 5:rs1044471 | 0.08 |  |  |  |  |  |
| CHFR | SNP 9:rs35011845 | 0.22 | 0.22 | 21.9501 | 15.0583 | 1.46 | 10.3748 |

FIG. 9

| Maternal-specific SNP alleles (Maternal: AB, Fetal: AA) | SNPs | Maternal allele/shared allele ratio | Average RNA-SNP ratio per gene | Placenta FPKM | Blood cell FPKM | Fold-difference (Blood cell/Placenta) | Plasma FPKM |
|---|---|---|---|---|---|---|---|
| AKAP16 | SNP 18:rs2108978 | 1.33 | 1.33 | 22.414 | 18.1324 | 1.24 | 11.7168 |
| EIF2S2 | SNP 37:rs4911406 | 1.25 | 1.25 | 39.3008 | 35.9748 | 1.09 | 65.1988 |
| JHDM1D | SNP 51:rs76676651 | 1.4 | 1.4 | 43.0656 | 26.1836 | 1.64 | 28.1734 |
|  | SNP 5:rs11022079 | 0.5 | 0.5 | 10.735 | 36.1867 | 0.3 | 10.3945 |
| USP47 | SNP 6:rs148238084 | 0.5 |  |  |  |  |  |
| PPP4R2 | SNP 40:rs61188513 | 1.09 | 1.09 | 80.3628 | 69.563 | 1.16 | 47.4149 |
|  | SNP 15:rs4779520 | 0.78 | 1.64 | 22.9283 | 10.6869 | 2.15 | 19.3486 |
| KLF13 | SNP 16:rs6493629 | 2.5 |  |  |  |  |  |
| FAM107B | SNP 4:rs11259151 | 2 | 2 | 24.1097 | 15.1776 | 1.59 | 30.5864 |
| APGL2 | SNP 39:rs132759 | 1.33 | 1.33 | 17.9996 | 12.0226 | 1.5 | 28.1601 |
|  | SNP 10:rs2389930 | 1.56 | 1.11 | 27.2282 | 29.7396 | 0.92 | 31.7672 |
| RAP2A | SNP 11:rs12873919 | 0.67 |  |  |  |  |  |
|  | SNP 1:rs117963129 | 4 | 3.37 | 48.3896 | 11.7589 | 4.11 | 35.3443 |
|  | SNP 2:rs1055184 | 5 |  |  |  |  |  |
| RIF1 | SNP 3:rs493446 | 1.12 |  |  |  |  |  |
| STX17A | SNP 48:rs56286238 | 1.33 | 1.33 | 61.0052 | 36.447 | 1.67 | 30.0074 |
|  | SNP 23:rs14031 | 0.5 | 0.62 | 11.0432 | 32.3155 | 0.34 | 8.3988 |
| C19orf63 | SNP 24:rs1046246 | 0.75 |  |  |  |  |  |
| SMEK1 | SNP 14:rs10135595 | 1 | 1 | 27.1212 | 33.0441 | 0.82 | 26.8366 |
|  | SNP 42:rs3797341 | 1.5 | 1.02 | 26.837 | 30.3427 | 0.88 | 45.4431 |
|  | SNP 43:rs3203972 | 0.78 |  |  |  |  |  |
| TNFAIP8 | SNP 44:rs1045242 | 0.79 |  |  |  |  |  |
| CPEB4 | SNP 46:rs12659398 | 1 | 1 | 28.4523 | 40.5723 | 0.7 | 28.802 |
| PTPRJ | SNP 7:rs117902837 | 2 | 2 | 59.7568 | 20.5437 | 2.91 | 19.0642 |
| RPL36 | SNP 22:rs3810220 | 1.7 | 1.7 | 152.2501 | 65.9528 | 2.31 | 921.8925 |
|  | SNP 25:rs1137288 | 1.62 | 1.88 | 114.7107 | 41.6233 | 2.76 | 176.8333 |
|  | SNP 26:rs3087895 | 2.17 |  |  |  |  |  |
|  | SNP 27:rs3768670 | 1.86 |  |  |  |  |  |
| YPEL5 | SNP 28:rs3768671 | 1.86 |  |  |  |  |  |
|  | SNP 53:rs114261839 | 1 | 1.33 | 51.7974 | 43.9599 | 1.18 | 30.1847 |
|  | SNP 54:rs208753 | 1.4 |  |  |  |  |  |
|  | SNP 55:rs17635381 | 2.27 |  |  |  |  |  |
| PCM1 | SNP 56:rs6991775 | 0.67 |  |  |  |  |  |
| U8R2 | SNP 47:rs6916713 | 2.25 | 2.25 | 102.9892 | 23.2007 | 4.44 | 43.5569 |
|  | SNP 32:rs3747 | 1.22 | 1.97 | 50.467 | 37.5349 | 1.34 | 96.8859 |
|  | SNP 33:rs9579 | 2.17 |  |  |  |  |  |
|  | SNP 34:rs3088214 | 2.89 |  |  |  |  |  |
| TNS1 | SNP 35:rs1063281 | 1.62 |  |  |  |  |  |
| EIF4A1 | SNP 17:rs1057086 | 0.93 | 0.93 | 70.1974 | 132.2932 | 0.53 | 161.6599 |
| BACH1 | SNP 38:rs15092 | 2.5 | 2.5 | 112.4409 | 34.6219 | 3.25 | 26.4288 |
|  | SNP 49:rs6850 | 1.11 | 1.05 | 66.7742 | 62.9202 | 1.06 | 220.7639 |
| PPIA | SNP 50:rs6904 | 1 |  |  |  |  |  |
| TMX1 | SNP 12:rs7160810 | 1 | 1 | 11.8758 | 12.8978 | 0.92 | 6.7127 |
| ANKRD44 | SNP 29:rs3731569 | 3.67 | 3.67 | 65.5013 | 14.0504 | 4.66 | 16.412 |
|  | SNP 57:rs3398 | 0.33 | 1.51 | 43.1289 | 37.048 | 1.16 | 37.6685 |
| ZFAND5 | SNP 58:rs969 | 2.69 |  |  |  |  |  |
|  | SNP 19:rs12327477 | 0.67 | 3.89 | 171.6269 | 29.4281 | 5.83 | 25.153 |
|  | SNP 20:rs2304859 | 7 |  |  |  |  |  |
| SMCHD1 | SNP 21:rs7238459 | 4 |  |  |  |  |  |
| NR3C1 | SNP 45:rs6191 | 1 | 1 | 28.0561 | 36.5516 | 0.77 | 11.2138 |
| CRNKL1 | SNP 36:rs2255255 | 1.5 | 1.5 | 15.8244 | 13.148 | 1.2 | 19.1897 |
| CALM1 | SNP 13:rs5871 | 1.1 | 1.1 | 76.0647 | 89.0949 | 0.85 | 181.3474 |
| FDFT1 | SNP 52:rs79708434 | 1.56 | 1.56 | 83.9629 | 34.6215 | 2.43 | 44.9826 |
|  | SNP 30:rs1051677 | 1 | 1.17 | 74.6452 | 75.2029 | 0.99 | 55.8144 |
| XRCC5 | SNP 31:rs2440 | 1.33 |  |  |  |  |  |
|  | SNP 8:rs3741380 | 2.75 | 1.81 | 29.7293 | 14.0146 | 2.12 | 90.3776 |
| EHBP1L1 | SNP 9:rs591182 | 0.88 |  |  |  |  |  |
| OPA1 | SNP 41:rs7643844 | 1.5 | 1.5 | 49.1647 | 22.7367 | 2.16 | 34.8335 |

*FIG. 10*

| Maternal-specific SNP alleles (Maternal: AB, Fetal: AA) | 5641 (PET) (GA: 36 6/7) | | | 7171 (Normal) (GA: 36 6/7) | | | Fold-changes of RNA-SNP ratio for each gene (5641 vs 7171) | Expression level in the plasma | | Fold-changes of FPKM (5641 vs 7171) |
|---|---|---|---|---|---|---|---|---|---|---|
| | SNPs | Maternal allele/shared allele ratio | Average RNA-SNP ratio per gene | SNPs | Maternal allele/shared allele ratio | Average RNA-SNP ratio per gene | | 5641 FPKM | 7171 FPKM | |
| ANXA4 | SNP 1:kgp9682337 | 2 | 2 | SNP 9:rs6546548 | 0.5 | 0.5 | 4 | 12.1379 | 4.7565 | 2.551855356 |
| RAC2 | SNP 3:rs6572 | 0.75 | 0.75 | SNP 8:rs2239774 | 8 | 8 | 0.09375 | 319.973 | 288.0251 | 1.110928255 |
| TP53 | SNP 2:rs178879353 | 0.5 | 1.25 | SNP 4:rs1042522 | 0.5 | 0.5 | 2.5 | 28.9503 | 13.1548 | 2.200740414 |
| | SNP 4:rs1042522 | 2 | | | | | | | | |
| SLC4A1 | SNP 5:rs5035 | 1.8 | 1.8 | SNP 7:rs2072081 | 1 | 1 | 1.8 | 165.1352 | 192.3307 | 0.858600317 |
| ARHGDIB | SNP 6:kgp6869929 | 0.76 | 0.76 | SNP 6:kgp6869929 | 0.71 | 0.71 | 1.070422535 | 665.6615 | 640.9633 | 1.038532939 |

|  | Early pregnancy | | Late pregnancy | |
| --- | --- | --- | --- | --- |
|  | no. of SNPs | no. of genes[a] | no. of SNPs | no. of genes |
| *Fetal-specific SNP alleles (fetus=AB, mother=AA):* | | | | |
| Total informative SNPs/genes | 16,051 | 6,714 | 20,643 | 7,788 |
| SNPs/genes after ASE filtering | NA[b] | | 19,463 | 7,581 |
| Transcripts in maternal plasma | 4,470 | 2,647 (39.43%)[c] | 7,114 | 3,813 (48.96%) |
| Fetal contribution (total) | 109 | 98 (3.70%)[d] | 504 | 430 (11.28%) |
| High fetal contribution | 25 | 24 (0.91%)[e] | 112 | 96 (2.52%) |
| *Maternal-specific SNP alleles (fetus=AA, mother=AB):* | | | | |
| Total informative SNPs/genes | 15,962 | 6,753 | 19,833 | 7,761 |
| SNPs/genes after ASE filtering | NA | | 19,343 | 7,656 |
| Transcripts in maternal plasma | 4,414 | 2,654 (39.30%) | 6,995 | 3,717 (47.89%) |
| Maternal contribution (total) | 3,156 | 2,041 (76.90%) | 5,023 | 2,911 (78.32%) |
| High maternal contribution | 1,634 | 1,130 (42.58%) | 3,002 | 1,895 (50.98%) | a. Number of genes that contained informative SNPs.
b. Allele-specific expression (ASE) filtering was not performed for early pregnancy samples.
c. % of total informative genes that was present in maternal plasma.
d. % of maternal plasma transcripts contributed by fetus.
e. % of maternal plasma transcripts contributed highly by fetus.

*FIG. 16*

|  | Late pregnancy | |
|---|---|---|
|  | no. of SNPs | no. of genes[a] |
| *Fetal-specific SNP alleles (fetus=AB, mother=AA):* | | |
| Total informative SNPs/genes | 20,643 | 7,788 |
| Transcripts in maternal plasma | 7,303 | 3,839 (49.29%)[b] |
| Fetal contribution (total) | 581 | 485 (12.63%)[c] |
| High fetal contribution | 132 | 111 (2.89%)[d] |
| *Maternal-specific SNP alleles (fetus=AA, mother=AB):* | | |
| Total informative SNPs/genes | 19,833 | 7,761 |
| Transcripts in maternal plasma | 7,365 | 3,829 (49.34%) |
| Maternal contribution (total) | 5,326 | 3,014 (78.72%) |
| High maternal contribution | 3,321 | 1,986 (51.87%) | a. Number of genes that contained informative SNPs.
b. % of total informative genes that was present in maternal plasma.
c. % of maternal plasma transcripts contributed by fetus.
d. % of maternal plasma transcripts contributed highly by fetus.

*FIG. 17*

| GNAS (SNP locus: rs7121) | Genotyping | A-allele count (shared allele) | B-allele count (Maternal-specific) | Fractional maternal contribution, M = 2*Maternal allele/(Maternal+Fetal allele) | Fractional fetal contribution, F = 1-M | FPKM | | | |
|---|---|---|---|---|---|---|---|---|---|
| 7171 (Control) | Mother: AB, Fetus: AA | 7 | 6 | 0.92 | 0.08 | 310.3 | | | |

| GNAS (SNP locus: rs7121) | Genotyping | A-allele count (shared allele) | B-allele count (Fetal-specific) | Fractional fetal contribution, F = 2*Fetal allele/(Maternal+Fetal allele) | Fractional maternal contribution, M = 1-F | FPKM | % change in fractional maternal contribution vs control | % change in fractional fetal contribution vs control |
|---|---|---|---|---|---|---|---|---|
| 5641 (PET) | Mother: AA, Fetus: AB | 81 | 4 | 0.09 | 0.91 | 376.2 | (0.91-0.92)/(0.92)*100 = -1.09% | (0.09-0.08)/(0.08)*100 = +12.5% |

*FIG. 19*

| Gene | Case 9355 | | | Case 9415 | | | Remark (references) |
|---|---|---|---|---|---|---|---|
| | Pre-delivery plasma (transcript level) | Post-delivery plasma (transcript level) | Fold-change | Pre-delivery plasma (transcript level) | Post-delivery plasma (transcript level) | Fold-change | |
| CSH1 | 1391.00 | 17.66 | 78.78 | 796.21 | 1.13 | 704.89 | a (1) |
| KISS1 | 433.89 | 8.25 | 52.56 | 147.36 | 7.26 | 20.29 | a (2) |
| STAT1 | 227.34 | 104.49 | 2.18 | 275.22 | 85.30 | 3.23 | b |
| CGA | 270.02 | 6.98 | 38.67 | 134.19 | 1.00 | 134.19 | |
| CSH2 | 136.04 | 3.89 | 34.96 | 185.78 | 2.74 | 67.84 | |
| TFPI2 | 216.09 | 15.11 | 14.30 | 85.16 | 3.55 | 24.02 | a (2) |
| GBP1 | 99.47 | 45.89 | 2.17 | 153.00 | 63.58 | 2.41 | b |
| PLAC4 | 177.67 | 1.03 | 172.41 | 69.32 | 1.00 | 69.32 | a (3) |
| HSD17B1 | 140.14 | 5.94 | 23.58 | 93.76 | 25.56 | 3.67 | b |
| CSHL1 | 140.57 | 1.00 | 140.57 | 66.97 | 1.00 | 66.97 | a (4) |
| KRT8 | 86.47 | 23.42 | 3.69 | 76.78 | 13.28 | 5.78 | c |
| KRT18 | 86.76 | 25.92 | 3.35 | 64.11 | 20.27 | 3.16 | b |
| HPGD | 87.76 | 38.45 | 2.28 | 39.05 | 13.36 | 2.92 | d |
| GADD45G | 48.82 | 20.75 | 2.35 | 73.22 | 23.37 | 3.13 | b |
| LGALS14 | 56.55 | 1.00 | 56.55 | 62.86 | 1.00 | 62.86 | |
| HSD3B1 | 60.62 | 3.51 | 17.28 | 48.26 | 1.00 | 48.26 | |
| KRT19 | 77.95 | 24.04 | 3.24 | 30.71 | 3.52 | 8.71 | |
| SERPINE1 | 37.39 | 15.29 | 2.45 | 60.90 | 12.71 | 4.79 | a (5) |
| GDF15 | 62.32 | 3.68 | 16.92 | 33.52 | 12.10 | 2.77 | |
| CYP19A1 | 70.84 | 4.90 | 14.47 | 18.65 | 1.00 | 18.65 | |
| PSG4 | 36.10 | 1.45 | 24.89 | 47.82 | 1.00 | 47.82 | |
| PSG3 | 53.00 | 1.00 | 53.00 | 23.03 | 1.00 | 23.03 | |
| CRYAB | 15.46 | 1.00 | 15.46 | 58.22 | 4.50 | 12.93 | |
| HSPB8 | 35.57 | 6.62 | 5.37 | 36.79 | 13.47 | 2.73 | |
| PKIB | 45.08 | 8.79 | 5.13 | 26.12 | 8.09 | 3.23 | |
| PGF | 44.72 | 5.40 | 8.29 | 24.94 | 3.80 | 6.57 | |
| CYP11A1 | 40.77 | 3.64 | 11.20 | 28.04 | 1.71 | 16.41 | |
| PSG5 | 42.56 | 1.00 | 42.56 | 25.66 | 1.00 | 25.66 | |
| PSG1 | 37.70 | 1.49 | 25.29 | 28.17 | 1.00 | 28.17 | |
| PAPPA | 40.90 | 5.91 | 6.92 | 20.93 | 1.00 | 20.93 | a (6) |
| ADAM12 | 44.48 | 4.01 | 11.09 | 15.16 | 1.00 | 15.16 | a (7) |
| PSG2 | 29.16 | 1.00 | 29.16 | 29.95 | 1.00 | 29.95 | |
| VGLL3 | 34.80 | 1.98 | 17.54 | 20.36 | 1.80 | 11.34 | |
| KRT7 | 27.20 | 10.39 | 2.62 | 26.54 | 9.75 | 2.72 | |
| TMEM54 | 32.99 | 5.94 | 5.56 | 18.70 | 5.22 | 3.58 | |
| PRKCZ | 28.22 | 10.05 | 2.81 | 23.12 | 8.76 | 2.64 | |
| SDC1 | 30.62 | 2.62 | 11.68 | 17.43 | 1.84 | 9.45 | |
| LGALS13 | 32.32 | 1.00 | 32.32 | 15.60 | 1.00 | 15.60 | |
| EFHD1 | 15.55 | 2.80 | 5.56 | 30.55 | 3.94 | 7.76 | |
| CAPN6 | 23.18 | 1.64 | 14.14 | 22.90 | 1.00 | 22.90 | |
| XAGE3 | 25.08 | 2.59 | 9.67 | 13.08 | 1.00 | 13.08 | |
| EBI3 | 18.79 | 6.48 | 2.90 | 17.96 | 7.30 | 2.46 | |
| GH2 | 19.16 | 1.00 | 19.16 | 17.22 | 1.00 | 17.22 | a (7) |
| PAGE4 | 28.69 | 2.99 | 9.67 | 6.28 | 1.00 | 6.28 | |

FIG. 21

| Gene | Case 9356 | | | Case 9415 | | | Remark (references) |
|---|---|---|---|---|---|---|---|
| | Pre-delivery plasma (transcript level) | Post-delivery plasma (transcript level) | Fold-change | Pre-delivery plasma (transcript level) | Post-delivery plasma (transcript level) | Fold-change | |
| ALPP | 19.62 | 1.54 | 12.73 | 14.03 | 1.00 | 14.03 | |
| INHBA | 18.99 | 2.71 | 7.01 | 14.51 | 4.29 | 3.38 | a (6) |
| LOC100505659 | 17.53 | 1.00 | 17.53 | 15.65 | 1.00 | 15.65 | |
| FBLN1 | 10.12 | 2.12 | 4.76 | 20.01 | 1.28 | 15.62 | |
| SEMA3B | 16.06 | 2.52 | 6.38 | 12.90 | 1.00 | 12.90 | |
| GPC3 | 18.22 | 1.00 | 18.22 | 10.12 | 1.00 | 10.12 | |
| PLAC2 | 19.86 | 1.99 | 9.96 | 8.04 | 1.97 | 4.09 | |
| PSG9 | 7.10 | 1.00 | 7.10 | 20.32 | 1.00 | 20.32 | a (8) |
| FN1 | 17.30 | 6.57 | 2.63 | 9.72 | 3.81 | 2.55 | |
| NOS3 | 10.01 | 3.45 | 2.90 | 16.07 | 7.08 | 2.27 | |
| LOC100506655 | 12.29 | 1.00 | 12.29 | 13.53 | 1.00 | 13.53 | |
| PSG11 | 19.48 | 1.83 | 10.63 | 5.77 | 1.00 | 5.77 | |
| SPTLC3 | 19.82 | 1.00 | 19.82 | 4.99 | 1.00 | 4.99 | |
| EXPH5 | 12.58 | 4.48 | 2.81 | 12.09 | 2.24 | 5.40 | |
| HSPA2 | 12.86 | 5.85 | 2.20 | 11.40 | 4.87 | 2.34 | |
| PSG6 | 10.66 | 1.00 | 10.66 | 13.38 | 1.00 | 13.38 | |
| PLAC1 | 17.08 | 1.00 | 17.08 | 6.60 | 1.00 | 6.60 | a (3) |
| TACC2 | 5.93 | 1.61 | 3.69 | 16.24 | 1.64 | 9.89 | |
| PRPF40B | 8.27 | 3.98 | 2.08 | 12.53 | 5.32 | 2.36 | |
| LOC388948 | 12.97 | 1.00 | 12.97 | 7.71 | 1.00 | 7.71 | |
| SERPINB2 | 13.48 | 1.36 | 9.91 | 6.86 | 1.44 | 4.77 | a (9) |
| CRH | 15.40 | 1.00 | 15.40 | 4.75 | 1.00 | 4.75 | a (10) |
| GBP1P1 | 6.35 | 1.19 | 5.32 | 13.04 | 5.04 | 2.59 | |
| CLDN4 | 12.50 | 1.00 | 12.50 | 6.45 | 2.84 | 2.27 | |
| C2orf72 | 11.14 | 3.29 | 3.38 | 7.26 | 1.74 | 4.18 | |
| PAPPA2 | 10.92 | 1.53 | 7.13 | 7.48 | 1.00 | 7.48 | |
| HIST2H3A | 14.75 | 7.27 | 2.03 | 2.44 | 1.02 | 2.39 | |
| HIST2H3C | 14.75 | 7.27 | 2.03 | 2.44 | 1.02 | 2.39 | |
| TCL6 | 12.92 | 1.00 | 12.92 | 3.93 | 1.00 | 3.93 | |
| MFSD2A | 8.09 | 3.35 | 2.42 | 8.72 | 1.00 | 8.72 | |
| ZFAT-AS1 | 9.10 | 3.14 | 2.90 | 7.25 | 3.31 | 2.19 | |
| INSL4 | 13.90 | 2.40 | 5.80 | 2.01 | 1.00 | 2.01 | |
| DHRS2 | 12.24 | 6.11 | 2.00 | 3.30 | 1.00 | 3.30 | |
| HES2 | 11.03 | 3.11 | 3.54 | 4.50 | 1.46 | 3.08 | |
| WLS | 11.06 | 4.77 | 2.32 | 4.40 | 1.68 | 2.63 | |
| PLCXD3 | 10.49 | 3.62 | 2.90 | 4.88 | 2.01 | 2.43 | |
| LOC100505483 | 5.40 | 1.00 | 5.40 | 9.39 | 2.62 | 3.58 | |
| C1orf130 | 11.60 | 1.85 | 6.28 | 2.48 | 1.00 | 2.48 | |
| FOSB | 3.02 | 1.00 | 3.02 | 10.65 | 4.94 | 2.16 | |
| GCM1 | 5.93 | 1.60 | 3.71 | 6.94 | 1.00 | 6.94 | a (8) |
| TRPV6 | 9.31 | 1.00 | 9.31 | 3.41 | 1.00 | 3.41 | |
| TFAP2A | 4.02 | 1.00 | 4.02 | 8.59 | 1.46 | 5.87 | |
| MMP11 | 10.08 | 1.96 | 5.16 | 2.46 | 1.00 | 2.46 | |
| TUSC3 | 9.90 | 2.66 | 3.73 | 2.55 | 1.00 | 2.55 | |
| HMGCR | 7.15 | 2.25 | 3.18 | 5.13 | 2.26 | 2.27 | |

*FIG. 21 cont.*

| Gene | Case 9356 | | | Case 9415 | | | Remark (references) |
|---|---|---|---|---|---|---|---|
| | Pre-delivery plasma (transcript level) | Post-delivery plasma (transcript level) | Fold-change | Pre-delivery plasma (transcript level) | Post-delivery plasma (transcript level) | Fold-change | |
| CCK | 7.06 | 1.00 | 7.06 | 4.98 | 1.00 | 4.98 | |
| LOC100129935 | 8.56 | 1.61 | 5.32 | 3.38 | 1.00 | 3.38 | |
| C8orf39 | 4.02 | 1.00 | 4.02 | 7.66 | 2.93 | 2.69 | |
| GLDN | 9.39 | 1.00 | 9.39 | 2.44 | 1.00 | 2.44 | |
| PGAP3 | 6.10 | 2.19 | 2.78 | 4.84 | 2.32 | 2.09 | |
| MSX2P1 | 3.63 | 1.00 | 3.63 | 6.87 | 3.38 | 2.05 | |
| GH1 | 4.33 | 1.00 | 4.33 | 6.02 | 1.00 | 6.02 | |
| SVEP1 | 7.79 | 2.98 | 2.61 | 2.26 | 1.00 | 2.26 | |
| PPP1R32 | 2.78 | 1.00 | 2.78 | 7.24 | 1.35 | 5.37 | |
| PSG8 | 5.01 | 1.00 | 5.01 | 4.94 | 1.00 | 4.94 | |
| ENDOU | 7.24 | 2.40 | 3.02 | 2.27 | 1.00 | 2.27 | |
| EGFR | 6.83 | 1.00 | 6.83 | 2.54 | 1.00 | 2.54 | |
| DUSP4 | 5.24 | 1.61 | 3.26 | 4.13 | 1.41 | 2.92 | |
| PHYHIPL | 5.53 | 1.00 | 5.53 | 3.48 | 1.39 | 2.51 | |
| CTSF | 6.01 | 1.00 | 6.01 | 2.77 | 1.03 | 2.69 | |
| TRIM29 | 3.54 | 1.00 | 3.54 | 5.13 | 1.00 | 5.13 | |
| RCN3 | 3.07 | 1.00 | 3.07 | 5.34 | 1.12 | 4.77 | |
| SPIRE2 | 5.93 | 2.27 | 2.61 | 2.48 | 1.00 | 2.48 | |
| LOC100216001 | 4.60 | 1.06 | 4.35 | 3.55 | 1.49 | 2.39 | |
| FAM176A | 5.76 | 2.10 | 2.74 | 2.36 | 1.00 | 2.36 | |
| SCIN | 5.18 | 1.00 | 5.18 | 2.82 | 1.00 | 2.82 | |
| ZNF500 | 2.41 | 1.00 | 2.41 | 5.52 | 2.23 | 2.47 | |
| PRR16 | 2.83 | 1.00 | 2.83 | 4.91 | 1.18 | 4.18 | |
| LOC100128054 | 4.55 | 1.05 | 4.35 | 3.08 | 1.00 | 3.08 | |
| OLR1 | 4.53 | 1.17 | 3.87 | 2.71 | 1.00 | 2.71 | |
| SLC30A2 | 5.18 | 1.00 | 5.18 | 2.90 | 1.00 | 2.90 | |
| LOC285972 | 3.49 | 1.00 | 3.49 | 3.64 | 1.02 | 3.56 | |
| HESX1 | 4.25 | 1.26 | 3.38 | 2.64 | 1.00 | 2.64 | |
| TMEM139 | 4.61 | 1.00 | 4.61 | 2.25 | 1.00 | 2.25 | |
| ZNF727 | 3.82 | 1.00 | 3.82 | 2.58 | 1.24 | 2.09 | |
| TM4SF19 | 4.04 | 1.39 | 2.90 | 2.34 | 1.00 | 2.34 | |
| EFS | 3.88 | 1.00 | 3.88 | 2.38 | 1.00 | 2.38 | |
| TIMD4 | 2.08 | 1.00 | 2.08 | 3.62 | 1.51 | 2.39 | |
| ALDH3B2 | 2.91 | 1.00 | 2.91 | 2.76 | 1.00 | 2.76 | |
| KRT81 | 2.61 | 1.00 | 2.61 | 2.92 | 1.00 | 2.92 | |
| MUC15 | 2.94 | 1.00 | 2.94 | 2.19 | 1.00 | 2.19 | |
| PRSS8 | 2.20 | 1.00 | 2.20 | 2.87 | 1.00 | 2.87 | |
| SH2D5 | 2.41 | 1.00 | 2.41 | 2.42 | 1.00 | 2.42 | |
| LOC728175 | 2.28 | 1.00 | 2.28 | 2.31 | 1.10 | 2.09 | |
| GRHL2 | 2.45 | 1.00 | 2.45 | 2.13 | 1.00 | 2.13 | |
| PABPN1L | 2.18 | 1.00 | 2.18 | 2.37 | 1.00 | 2.37 | |
| CORO6 | 2.08 | 1.00 | 2.08 | 2.07 | 1.00 | 2.07 | |

Remark:
a. Transcripts previously reported to be pregnancy-associated in maternal plasma
b. Transcripts newly identified in this study by maternal plasma RNA-seq and validated by real-time RT-PCR (Supplemental Data Fig. 6)
c. KRT8 mRNA was not studied by real-time RT-PCR as the detection assay cannot be designed
d. Real-time RT-PCR result showed that maternal plasma HPGD mRNA did not show clearance pattern after delivery (Supplemental Data Fig. 6)

References:
1. Ng EKO, Tsui NBY, Lau TK, Leung TN, Chiu RWK, Panesar NS, et al. Proc Natl Acad Sci U S A 2003;100:4748-53.
2. Tsui NBY, Chim SSC, Chiu RWK, Lau TK, Ng EKO, Leung TN, et al. J Med Genet 2004;41:461-7.
3. Lo YMD, Tsui NBY, Chiu RWK, Lau TK, Leung TN, Heung MMS, et al. Nat Med 2007;13:218-23.
4. Heung MMS, Jin S, Tsui NBY, Ding C, Leung TY, Lau TK, et al. PLoS One 2009;4:e5858.
5. Purwosunu Y, Sekizawa A, Koide K, Farina A, Wibowo N, Wiknjosastro GH, et al. Clin Chem 2007;53:399-404.
6. Wong BCK, Chiu RWK, Tsui NBY, Chan KCA, Chan LW, Lau TK, et al. Clin Chem 2005;51:1786-95.
7. Pang WW, Tsui MHY, Sahota D, Leung TY, Lau TK, Lo YMD, Chiu RWK. Prenat Diagn 2009;29:495-504.
8. Go AT, Visser A, Mulders MA, Blankenstein MA, Van Vugt JM, Oudejans CB. Clin Chem 2004;50:1413-4.
9. Tsui NBY, Wong BCK, Leung TY, Lau TK, Chiu RWK, Lo YMD. Prenat Diagn 2009;29:1031-7
10. Ng EKO, Leung TN, Tsui NBY, Lau TK, Panesar NS, Chiu RWK, Lo YMD. Clin Chem 2003;49:727-31.

*FIG. 21 cont.*

| RNAs | Preeclampsia | Normal | RNAs | Preeclampsia | Normal |
|---|---|---|---|---|---|
| ADAM9 | 26.78 | 11.26 | LY6E | 84.52 | 31.38 |
| AGBL5 | 144.47 | 65.14 | MEIS1 | 79.49 | 18.77 |
| APOBR | 64.12 | 26.31 | MLH3 | 150.61 | 36.10 |
| APOL2 | 59.24 | 29.05 | MYADM | 51.11 | 16.60 |
| APP | 212.58 | 84.93 | NCF1 | 107.35 | 41.90 |
| ASAH1 | 167.14 | 47.38 | NCF1B | 34.80 | 9.41 |
| ATP5I | 23.85 | 9.20 | NDUFA1 | 20.73 | 7.36 |
| ATP6V0E1 | 60.73 | 20.56 | NES | 176.78 | 58.83 |
| B2M | 1765.75 | 654.19 | NFAM1 | 49.17 | 17.91 |
| BCAP31 | 42.85 | 14.86 | NGFRAP1 | 106.72 | 19.52 |
| BRK1 | 91.46 | 41.63 | NPTN | 80.63 | 29.97 |
| C12orf76 | 16.97 | 4.56 | NT5C3 | 173.39 | 65.34 |
| C19orf59 | 22.94 | 6.42 | OST4 | 404.86 | 100.63 |
| C19orf79 | 13.22 | 3.00 | PARK7 | 97.39 | 40.79 |
| C1orf151-NBL1 | 25.89 | 11.19 | PARP10 | 52.41 | 19.75 |
| C21orf7 | 308.80 | 83.41 | PDGFA | 55.19 | 24.29 |
| C7orf53 | 8.04 | 0.73 | PF4 | 680.43 | 208.45 |
| CARD16 | 85.90 | 29.13 | PGRMC1 | 332.76 | 78.90 |
| CD97 | 59.09 | 28.74 | PRIC285 | 72.34 | 20.44 |
| CEBPD | 147.37 | 44.30 | PSMB9 | 73.17 | 34.36 |
| CTSA | 341.67 | 138.37 | RAB32 | 51.90 | 25.20 |
| CYB5R1 | 25.14 | 10.12 | RABAC1 | 25.10 | 7.80 |
| DDX11L10 | 38.97 | 7.34 | RBX1 | 36.44 | 15.06 |
| DUSP1 | 168.06 | 30.57 | RNF213 | 316.69 | 147.00 |
| DYNLRB1 | 166.30 | 59.63 | RPPH1 | 242.37 | 63.73 |
| EMP3 | 99.80 | 39.75 | S100P | 48.92 | 14.31 |
| ENKUR | 64.87 | 15.45 | S1PR3 | 9.45 | 1.41 |
| GALM | 31.68 | 5.09 | SAT1 | 213.55 | 100.86 |
| GDI1 | 91.22 | 41.05 | SEPT3 | 14.54 | 6.35 |
| HIST1H2AC | 271.60 | 72.77 | SERF2 | 310.66 | 144.79 |
| HIST1H3H | 131.91 | 40.96 | SHISA5 | 141.53 | 59.85 |
| HIST1H4A | 20.40 | 5.53 | SIGLEC1 | 18.55 | 3.32 |
| HIST1H4B | 25.44 | 5.58 | SIGLEC14 | 10.79 | 0.95 |
| HIST1H4E | 74.16 | 26.59 | SNN | 348.09 | 171.73 |
| HIST1H4H | 69.35 | 18.31 | SOD2 | 569.41 | 229.85 |
| HIST1H4L | 20.99 | 6.89 | SPARC | 914.92 | 286.17 |
| HLA-C | 417.81 | 203.10 | TIMP1 | 76.27 | 27.68 |
| HLA-L | 11.78 | 3.90 | TMEM140 | 121.93 | 29.08 |
| HRC | 14.87 | 0.16 | TMEM185A | 36.93 | 12.09 |
| HSPA1A | 37.29 | 14.90 | TMEM50A | 139.68 | 32.72 |
| IFI6 | 171.27 | 18.29 | TRIM22 | 135.78 | 58.79 |
| ISG20 | 86.19 | 23.09 | TSC22D3 | 330.23 | 108.27 |
| JAM3 | 121.57 | 52.31 | UBE2L6 | 171.88 | 63.40 |
| KLF6 | 127.12 | 62.64 | VKORC1L1 | 63.06 | 25.17 |
| LEPR | 43.19 | 17.71 | VTRNA1-1 | 7.23 | 0.08 |
| LEPROT | 70.13 | 34.38 | YIF1B | 36.33 | 16.96 |
| LILRA5 | 31.45 | 11.05 | YPEL3 | 150.75 | 73.23 |
| LOC146336 | 13.75 | 4.89 | YWHAH | 236.85 | 116.18 |
| LRRC32 | 102.05 | 34.23 | ZNF485 | 15.35 | 6.38 |

*FIG. 26*

| PAPPA SNP rsID | DNA genotype | | Placenta | | Maternal blood cells | | Pre-delivery maternal plasma | | Post-delivery maternal plasma | |
|---|---|---|---|---|---|---|---|---|---|---|
| | Fetus | Mother | A | G | A | G | A | G | A | G |
| rs386088 | GA | AA | 2421 | 2164 | 0 | 0 | 16 | 21 | 0 | 0 |

FIG. 27

| H19 SNP rsID | DNA genotype | | Placenta | | Maternal blood cells | | Pre-delivery maternal plasma | | Post-delivery maternal plasma | |
|---|---|---|---|---|---|---|---|---|---|---|
| | Fetus | Mother | Shared | Maternal-specific | Shared | Maternal-specific | Shared | Maternal-specific | Shared | Maternal-specific |
| rs2839698[a] | AA | AG | 3418 (A) | 10 (G) | 0 (A) | 0 (G) | 246 (A) | 1679 (G) | 0 (A) | 808 (G) |
| rs2839701 | GG | CG | 4959 (G) | 8 (C) | 0 (G) | 0 (C) | 33 (G) | 219 (C) | 1 (G) | 78 (C) |
| rs2839702 | CC | AC | 4996 (C) | 8 (A) | 0 (C) | 0 (A) | 38 (C) | 233 (A) | 2 (C) | 92 (A) |
| rs3741219 | GG | AG | 2255 (G) | 15 (A) | 0 (G) | 0 (A) | 17 (G) | 158 (A) | 0 (G) | 96 (A) | a: The shared A-allele was imprinted while the maternal-specific G-allele was transcribed. Details of the methylation status are shown in Supplemental Data Fig. 5.

FIG. 28

MATERNAL PLASMA TRANSCRIPTOME ANALYSIS BY MASSIVELY PARALLEL RNA SEQUENCING

CROSS-REFERENCES TO RELATED APPLICATIONS

The present application claims priority to U.S. Provisional Patent Application No. 61/770,985, entitled "MATERNAL PLASMA TRANSCRIPTOME ANALYSIS BY MASSIVELY PARALLEL RNA SEQUENCING" and filed Feb. 28, 2013, which is incorporated herein by reference for all purposes.

BACKGROUND

Extracellular RNA molecules that are pregnancy-specific in maternal plasma have been reported[1]. They have provided a noninvasive testing tool for fetal assessment and pregnancy monitoring by simply using a peripheral blood specimen from the mother. To date, a number of promising prenatal diagnostic applications have been developed using maternal plasma RNA[2-8]. Researchers have been actively searching for additional RNA markers in order to extend the applications in different contexts of fetal disorders and pregnancy pathologies.

Theoretically, the most straightforward RNA marker identification method is to directly profile extracellular RNA molecules in maternal plasma. This method has not however been easy because conventional high-throughput screening technologies, such as microarray analysis and serial analysis of gene expression (SAGE), have a limited ability to detect the typically low concentrations of partially degraded extracellular RNA in maternal plasma[9]. Instead, most of the reported RNA marker screening strategies operate indirectly by comparing the expression profiles of the placenta and the maternal blood cells[10]. Only the transcripts that are expressed much higher in the placenta than in the maternal blood cells are further studied in maternal plasma samples by high sensitivity but low-throughput technologies, such as real-time reverse transcriptase polymerase chain reaction (RT-PCR). Thus far plasma RNA markers identified by this indirect method are relatively limited. This is possibly because the tissue-based mining strategy has not fully taken into account all of the biological factors influencing placental RNA levels in maternal plasma. In addition, transcripts that are expressed and released by non-placental tissues in response to pregnancy could not be identified by this method. A sensitive and high-throughput methodology that allows the direct profiling of the maternal plasma transcriptome would therefore be very desirable.

Similarly, direct plasma RNA profiling may be useful in other scenarios where there is a mixture of RNA molecules from two individuals, such as for organ transplantation. The circulation of transplantation recipients contains nucleic acid molecules from both the donor and recipient. A change in the relative profile of RNA molecules contributed by the donor or the recipient may reveal pathologies in the transplanted organ or recipient, such as graft rejection.

BRIEF SUMMARY

Methods, systems, and apparatuses are provided for diagnosing pregnancy-associated disorders, determining allelic ratios, determining maternal or fetal contributions to circulating transcripts, and/or identifying maternal or fetal markers using a sample from a pregnant female subject. In some embodiments, the sample is blood plasma containing a mixture of maternal- and fetal-derived RNA molecules.

The RNA molecules are analyzed (e.g., sequenced) to obtain a plurality of reads, and the locations of these reads in a reference sequence are identified (e.g., by sequence alignment). Informative loci are identified that are homozygous for a first allele in either the mother or fetus, and heterozygous for a first allele and a second allele in the other one of the mother and fetus. The informative loci are then filtered and reads located at (e.g., aligning to) the filtered informative loci are further analyzed. In some embodiments, a ratio of reads corresponding to first alleles and second alleles is calculated and compared to a cutoff to diagnose a pregnancy-associated disorder. In some embodiments, a portion of RNA in the sample that is of fetal origin is determined using reads located at filtered informative maternal loci. In some embodiments, a ratio of reads corresponding to the first allele and the second allele is calculated for an individual filtered informative locus, and the ratio is compared to a cutoff to designate the locus as a maternal or fetal marker.

The present methods are not limited to prenatal diagnostics and can be applied to any biological sample that contains a mixture of RNA molecules derived from two individuals. For example, a blood plasma sample obtained from an organ transplant recipient can be used. Transcripts expressed in the transplanted organ reflect the donor's genotype and occur at detectable levels in the recipient's blood. By reading these transcripts, informative loci within genes expressed by both the donor and recipient can be identified, and the relative expression levels of alleles from each individual can be measured. Abnormal expression levels of the allele contributed solely by the donor or recipient can be used to diagnose transplantation-associated disorders.

Biological samples that can be used in the present methods include blood, plasma, serum, urine, saliva and tissue samples. For example, fetal nucleic acids have been detected in the urine of pregnant women. The urine of recipients of kidney transplantation have been shown to contain cell-free nucleic acids and cells from the transplanted organ. Microchimerism has been observed in many conditions. Microchimerism refers to the presence of a source of cells or nucleic acids from another person in the body, including organs and tissues of a particular individual. Microchimerism has been observed in biopsies of the thyroid, liver, spleen, skin, bone marrow, and other tissues. Microchimerism may occur as a result of previous pregnancies, or blood transfusions.

Also provided is use of a gene for diagnosing a pregnancy-associated disorder in a pregnant female subject. The expression level of the gene is compared with a control value determined from one or more other female subjects, each pregnant with a healthy fetus. Pregnancy-associated disorders addressed herein include pre-eclampsia, intrauterine growth restriction, invasive placentation and pre-term birth. Other pregnancy-associated disorders may be conditions that place the fetus at risk of fetal demise, such as hemolytic disease of the newborn, placental insufficiency, hydrops fetalis, fetal malformation. Yet other pregnancy-associated diseases may be conditions that result in complications during pregnancy, such as the HELLP syndrome, systemic lupus erythematosus and other immunological diseases of the mother.

BRIEF DESCRIPTION OF THE DRAWINGS

FIGS. 4 and 5 show summaries of RNA-seq read alignment results.

FIG. 6A shows the GC % distribution of sequenced reads from the RNA-seq libraries of M9356P (with Ribo-Zero Gold pre-treatment) and M9415P (without Ribo-Zero Gold pre-treatment). FIG. 6B shows the correlation of gene expression profiles between M9356P and M9415P.

FIG. 9 shows RNA-SNP allelic ratios for fetal-specific SNP alleles and the expression levels of RNA transcripts containing these alleles in maternal plasma.

FIG. 10 shows RNA-SNP allelic ratios for maternal-specific SNP alleles and the expression levels of RNA transcripts containing these alleles in maternal plasma.

FIG. 11A shows RNA-SNP allelic ratios of case 5641 (third-trimester late-onset preeclampsia) and case 7171 (control) for informative SNPs comprising maternal-specific SNP alleles. FIG. 11B shows fold-differences of RNA-SNP allelic ratios and of plasma levels of case 5641 relative to those of 7171 (control) for informative SNPs comprising maternal-specific SNP alleles.

FIG. 12A shows RNA-SNP allelic ratios of case 5641 (third-trimester late-onset preeclampsia) and case 9356 (control) for informative SNPs comprising maternal-specific SNP alleles. FIG. 12B shows fold-differences of RNA-SNP allelic ratios and of plasma levels of case 5641 relative to those of 9356 for informative SNPs comprising maternal-specific SNP alleles.

FIG. 13 shows the data in FIGS. 11A and 11B in tabular form.

FIG. 14 shows the data in FIGS. 12A and 12B in tabular form.

FIG. 16 shows results of informative SNP analysis of the maternal plasma transcriptome.

FIG. 17 shows relative fetal and maternal contributions without allele-specific expression filtering in the maternal plasma samples of late pregnancy.

FIG. 18A shows proportions of fetal- and maternal-derived transcripts in the maternal plasma of early and late pregnancies. FIG. 18B shows allele counts and fetal-allele ratios before and after delivery.

FIG. 19 compares fractional fetal and maternal contributions at one RNA-SNP for pre-eclamptic and control pregnancy cases.

FIG. 21 is a list of pregnancy-associated genes.

FIG. 24A is a heatmap of gene expression ($\log_2$(transcript level)) of the placenta and maternal blood cells, as well as the pre- and post-delivery maternal plasma of the two late pregnancy cases. The 131 pregnancy-associated genes were preferentially expressed in the placenta. FIG. 24B shows that expression levels of the 131 genes in the placenta and in plasma were positively correlated (P<0.05, Spearman correlation).

FIG. 26 lists 98 preeclampsia-associated RNAs in maternal plasma as identified by RNA-Seq. The expression levels in the plasma collected from uncomplicated pregnant women and women who have developed preeclampsia are shown.

FIG. 27 shows RNA-sequencing read counts on single-nucleotide polymorphism (SNP) sites in PAPPA RNA for case 9415. Allele-A is the shared allele and allele-G is the fetal-specific allele.

FIG. 28 shows RNA-sequencing read counts on single-nucleotide polymorphism (SNP) sites in H19 RNA for case 9415.

DETAILED DESCRIPTION

I. Introduction

Figure 1:
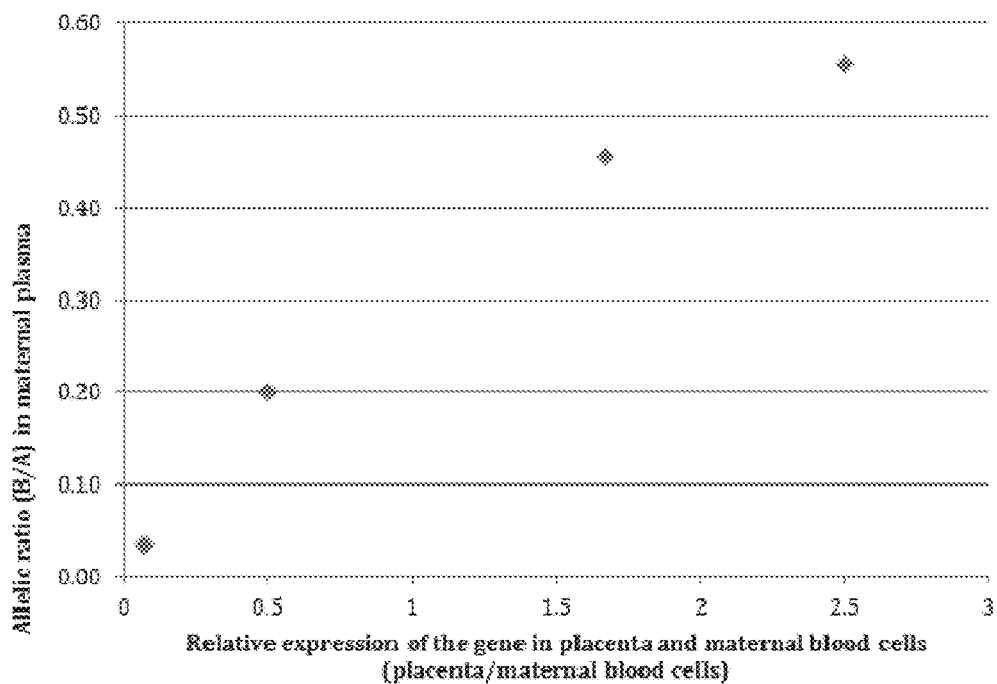
FIG. 1 shows a positive relationship between the allelic ratio B/A and the relative expression levels of the respective genes in placenta and maternal blood cells.

The presence of cell-free fetal RNA in maternal plasma was reported more than a decade ago[11]. Following this finding, many studies have since been conducted to detect circulating RNA of fetal and placental origin in maternal plasma[1,10,12] Interestingly, the expression levels of placenta-specific transcripts in the plasma were found to be positively correlated with those in placental tissues[10], underscoring the clinical utility of plasma RNA analysis as a noninvasive tool to monitor the placental or fetal health and development. Indeed, examination of maternal circulating RNA has found clinical applications for pregnancy- or placenta-related disorders such as preeclampsia[2,13-15], intrauterine growth retardation[4] and preterm birth[8], as well as for noninvasive testing of fetal chromosomal aneuploidies[5,7,16]. Such developments highlight the potential utilities of RNA biomarkers for the molecular assessment of prenatal disorders.

Despite the promising outlook of plasma RNA analysis in prenatal testing, there remain a limited number of well-validated pregnancy- or placenta-related transcripts in maternal plasma to date. In this regard, examination of RNA biomarkers in the plasma had been conducted using reverse transcriptase (RT)-PCR[1,4,8,10,12,13], a sensitive method that would typically target a relatively small number of RNA species per analysis. Of note, these studies mainly focused on genes with relatively high levels of expression in the placenta when compared with maternal blood cells, on the premise that pregnancy-associated genes are largely derived from the placenta. Such approaches have identified pregnancy-associated RNA targets that are highly expressed in the placenta, but might have missed other important targets. Furthermore, given the low concentrations and poor integrity of plasma RNA[9,15], conventional high-throughput methods such as serial analysis of gene expression and microarray analysis would not be robust for the direct examination of the plasma transcriptome.

The aforesaid technical limitations of plasma RNA analysis could potentially be resolved by employing massively parallel sequencing (MPS) for RNA analysis, namely RNA-sequencing (RNA-seq)[17, 18]. Given the enhanced sensitivity and wide dynamic range, RNA-seq has been employed to examine gene expression in many human tissues, including the placenta[19]. The superiority of MPS has been further demonstrated by its feasibility in direct profiling of plasma miRNAs in healthy individuals[20] and in pregnant women[21,22] Nevertheless, the full spectrum of plasma transcriptome remains elusive, which might be due to the lower stability of long RNA species compared to short miRNAs in the plasma[23].

In this study, we have shown that fetal- and maternal-derived transcripts can be detected in maternal plasma and that their relative contributions can be estimated using RNA-seq, by examination of fetal- and maternal-specific single-nucleotide polymorphisms (SNPs). In addition, the allele-specific expression patterns of the placenta can be monitored in maternal plasma. We have also demonstrated that pregnancy-associated transcripts could be identified by direct examination of the maternal plasma before and after delivery.

II. Method of Diagnosing a Pregnancy-Associated Disorder Using SNP Allelic Ratios The analysis of the gene expression profile is useful for the detection of the disease status of an individual. Embodiments of the present invention include methods to analyze the expression profile of an individual through the analysis of a mixture of RNA molecules from two different individuals. The methods make use of the relative abundances of alleles that are specific to one individual and the alleles shared between the two individuals. Based on the relative abundances of the shared and individual-specific alleles, the gene expression profiles of the two individuals can be determined. One possible application of the present methods is the analysis of the gene expression profile of a fetus by analysing the RNA in a maternal plasma sample which contains RNA from both the fetus and the pregnant woman. Another application is the analysis of the gene expression profile of donor-derived RNA in a plasma sample collected from a transplantation recipient that contains RNA from both the donor and recipient.

In a mixture containing RNA from two individuals, the expression profile of each individual cannot be determined based on the analysis of the total amount of the different RNA transcripts in the mixture because it is difficult to determine the relative contributions of each individual to the total RNA. The relative abundance of different RNA transcripts can be useful for monitoring of the well-being of an individual or to detect a disease state.

In this method, the genotype of the two individuals can first be determined either by direct genotyping of the individuals or by family analysis. For example, if the parents have the genotype of AA and TT, then the genotype of the fetus would be AT.

The following hypothetical example illustrates the principle of this method. For each of the gene of interest, there is a SNP within the coding region so that polymorphism can be observed in the RNA transcripts of the different genes. Assume that the genotypes of the fetus and the pregnant woman are AB and AA, respectively. Thus, the B allele would be specific for the fetus and the A allele would be shared between the fetus and the mother. The relative expression levels of the different genes in the placenta and the maternal blood cells are as shown in TABLE 1.

Figure 2:
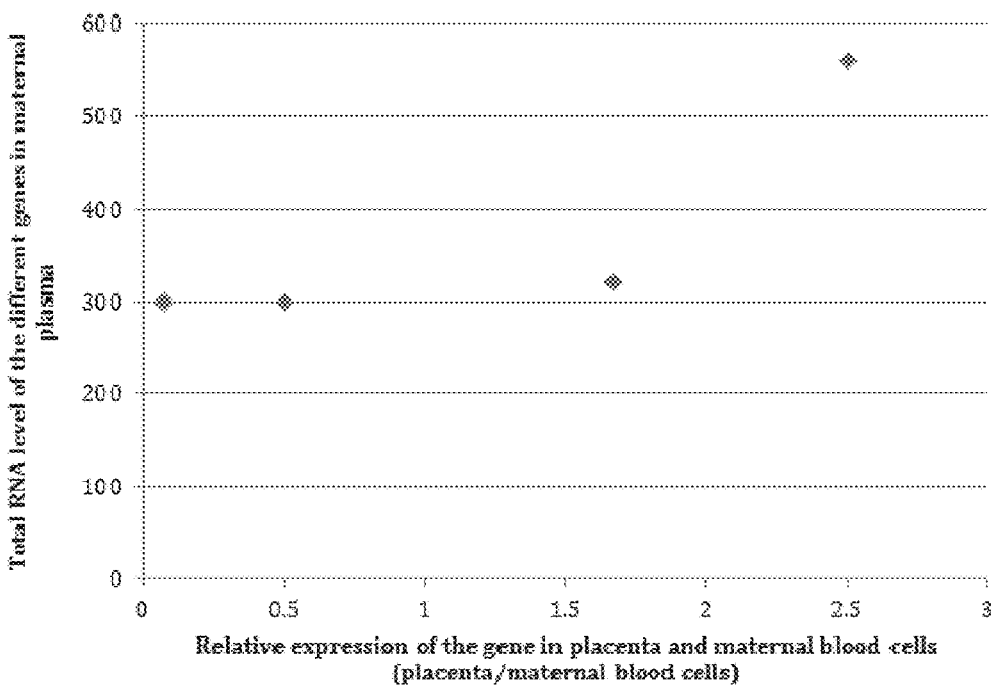
FIG. 2 shows a relationship between total gene expression level and the relative expression levels of genes in placenta and maternal blood cells.

In this example, we assume that the placenta and maternal blood cells would contribution a relative equal proportion of 2% of each of their RNA transcripts to the maternal plasma. In other words, if the placenta expression level of a gene is 10000, it would contribute 200 RNA transcripts of that gene to the maternal plasma. As shown in FIG. 1, the allelic ratio B/A shows a good positive relationship with the relative expression levels of the respective genes in placenta and maternal blood cells. In contrast, the total gene expression level is affected by the fluctuation of the expression of the maternal blood cells and hence, correlated less well with the expression of the placenta (FIG. 2).

TABLE 1

| Gene | Maternal genotype | Fetal genotype | Relative expression level in maternal blood cells | Relative expression level in the placenta | Relative expression (placenta/ maternal blood cells) | Relative abundance of maternal to fetal RNA | Maternal plasma Total RNA conc | Conc of RNA with the A allele | Conc of RNA with the B allele | B/A ratio |
|---|---|---|---|---|---|---|---|---|---|---|
| 1 | AA | AB | 8000 | 20000 | 2.5 | 1:1 | 560 | 360 | 200 | 0.56 |
| 2 | AA | AB | 6000 | 10000 | 1.67 | 1:1 | 320 | 220 | 100 | 0.45 |
| 3 | AA | AB | 10000 | 5000 | 0.5 | 1:1 | 300 | 250 | 50 | 0.2 |
| 4 | AA | AB | 14000 | 1000 | 0.071 | 1:1 | 300 | 290 | 10 | 0.03 |

Another advantage of using the allelic ratio analysis is that the expression level of a particular gene in the placenta is normalized to the expression level of the maternal blood cells. As the expression level can vary greatly across different genes and different samples, this normalization would make the comparison across different genes more robust and avoid the necessity of comparing to a reference gene, for example, a house keeping gene. In other words, in conventional gene expression analysis, level of expression of a gene in a sample is either measured with reference to a housekeeping gene or as an amount to the total RNA of the sample. To identify aberrant gene expression, conventionally, one would then compare those relative values of the test sample to the control samples.

Here we propose a new approach whereby we use the relative amounts contributed by the fetus normalized to the mother's contribution of the same gene as a means to determine the gene expression profile. In pathological states, for example preeclampsia, preterm labor, maternal diseases such as systemic erythematosus, whereby the expression of the gene in the placenta or maternal organs are altered, the fetal to maternal ratio of that gene would be altered when compared with pregnancies without such pathological conditions. This approach can be practised using the fetal-specific SNP allele relative to the shared allele among RNA transcripts in maternal plasma.

The approach can also be practised using the maternal-specific SNP allele relative to the shared allele among RNA transcripts in maternal plasma. Pathological conditions could be identified when one or more of such allelic ratios for one or more RNA gene transcripts are altered when compared to that expected for a non-pathological state. The pattern of such allelic ratios across a gene locus or multiple gene loci could be used to identify pathological states. Non-pathological states could be represented by the allelic ratios in normal pregnancies, in samples obtained before or after testing when the pregnancy is no longer affected by the pathological state or from existing data previously obtained from normal pregnancies, i.e. a previously derived reference range.

Pregnancy-associated disorders that can be diagnosed using the present methods include any disorders characterized by abnormal relative expression levels of genes in maternal and fetal tissue. These disorders include, but are not limited to, preeclampsia, intrauterine growth restriction, invasive placentation, pre-term birth, hemolytic disease of the newborn, placental insufficiency, hydrops fetalis, fetal malformation, HELLP syndrome, systemic lupus erythematosus, and other immunoligcal diseases of the mother. The methods distinguish between RNA molecules contributed by the mother and fetus in a sample that contains a mixture of such molecules. The methods can thus identify changes in the contribution from one individual (i.e., the mother or fetus) to the mixture at a particular locus or for a particular gene, even if the contribution from the other individual does not change or moves in the opposite direction. Such changes cannot be easily detected when measuring the overall expression level of the gene without regard to the tissue or individual of origin. Pregnancy-associated disorders, as discussed herein, are not characterized by chromosomal abnormalities in the fetus, for example aneuploidy.

The present methods can also be performed without prior genotyping information of the placenta. For example, the genotype of the pregnant woman can be determined by direct genotyping of her blood cells. Then, the RNA transcripts of the plasma samples can be analyzed, for example but not limited to massively parallel sequencing. RNA transcripts showing two different alleles can be identified. In this set of transcripts, if the mother is homozygous, it would indicate that the fetus is heterozygous for the fetal-specific allele and the maternal allele. In this scenario, the RNA allelic ratio analysis can be performed without prior genotype information of the fetus (or the placenta). Additionally, instances where the mother is heterozygous but the fetus is homozygous can be identified by a deviation from a 1:1 ratio. Further details of such techniques are described in U.S. Pat. No. 8,467,976.

A. Diagnostic Method

Figure 3:
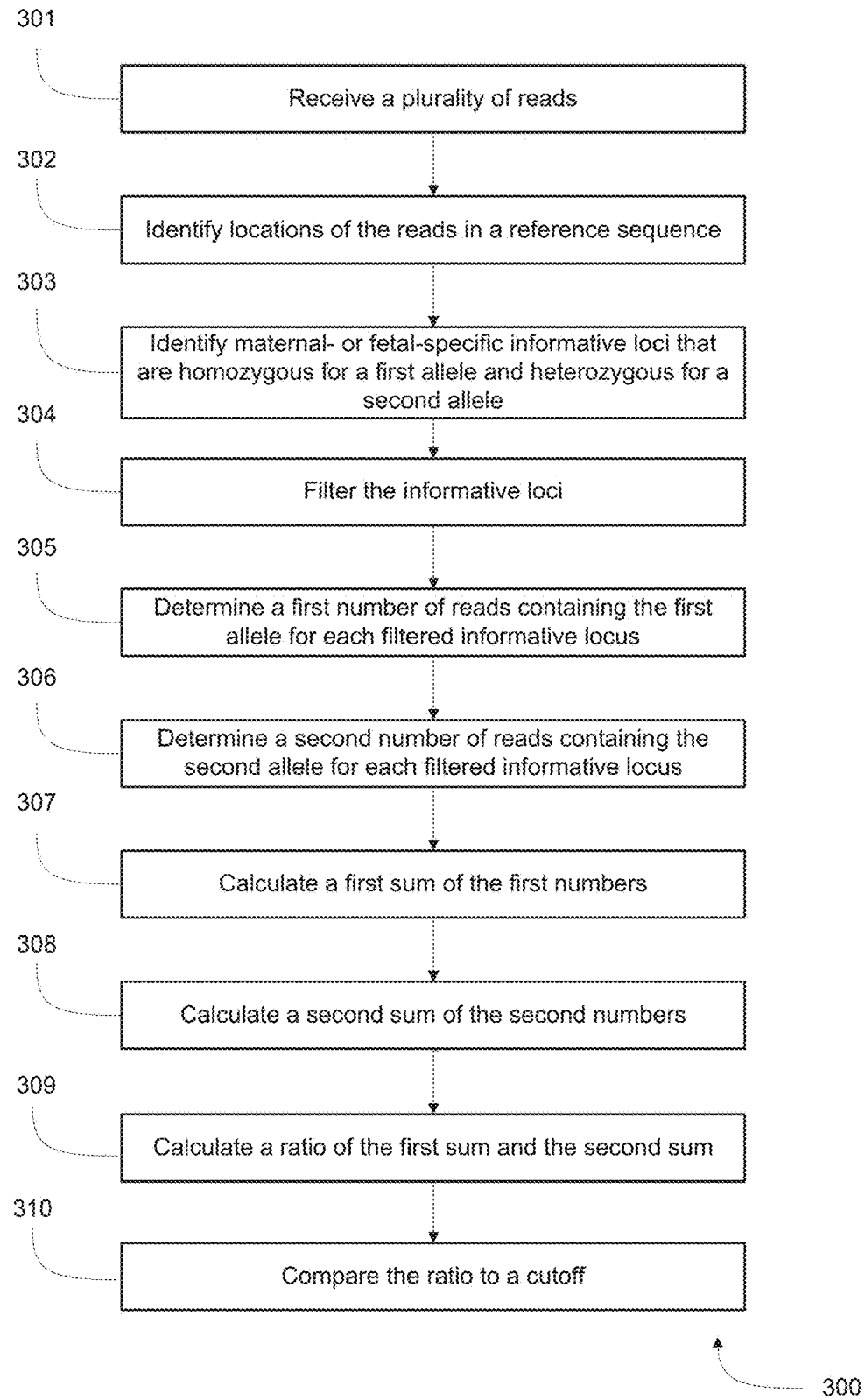
FIG. 3 is a flowchart for methods of diagnosing a pregnancy-associated disorder.

A method 300 for diagnosing a pregnancy-associated disorder according to some embodiments is shown in FIG. 3. The method uses a sample from a female subject pregnant with a fetus. The sample can be of maternal blood plasma and contains a mixture of maternal- and fetal-derived RNA molecules. The sample can be obtained as desired, from a female subject at any stage of pregnancy. For example, first-, second- and third-trimester pregnant women with singleton pregnancies can serve as subjects. First- and second-trimester pregnant women can be categorized as "early pregnancy cases" and third-trimester pregnant women can be categorized as "late pregnancy cases". In some embodiments, samples can also be collected after delivery of the fetus, or from the same subject before and after delivery, and samples from non-pregnant females can serve as controls. Samples can be obtained any time after delivery (for example, 24 hours).

The sample can be obtained from peripheral blood. A maternal blood sample can be processed as desired, for example by centrifguing to separate blood cells from plasma. Stablizers can be added the blood sample or portions thereof, and the sample can be stored before use. In some embodiments, samples of fetal tissue are also obtained, for example chorionic villi, amniotic fluid, or placental tissue. The fetal tissue can be used to determine fetal genotypes, as is discussed below. Fetal tissue can be obtained before or after delivery.

Once a sample is obtained, RNA or DNA can then be extracted from the maternal blood cells and plasma, as well as from any fetal tissue such as a sample of the placenta. Placental and blood cell RNA samples can be pre-treated, such as with the Ribo-Zero Gold Kit (Epicentre), to remove ribosomal RNA (rRNA) prior to sequencing library preparation.

In step 301 of the method, a plurality of reads is received. The reads are obtained from an analysis of RNA molecules obtained from the sample. In various embodiments, the reads can be obtained by sequencing, digital PCR, RT-PCR, and mass spectrometry. Although the discussion focuses on sequencing, aspects of the description are also applicable to other techniques for obtaining the reads. For example, digital PCR (including microfluidic and droplet PCR) can provide knowledge of different alleles at a particular locus using probes (including primers) directed to each allele. The probes can bear labels to make them distinguishable from each other, for example by exhibiting different colors. In the same experiment or in a different experiment (for example, on a separate slide or chip), probes with different labels can be directed to different loci. Detection of the labels reflects the presence and/or quantity of the RNA or cDNA molecules being amplified and corresponds to reads of the RNA or cDNA molecules, where such reads provide information about a sequence of the RNA or cDNA molecules at the loci corresponding to the probes. The description regarding "sequence reads" equally applies to reads obtained via any suitable technique, including non-sequencing techniques.

Sequencing can be performed as desired, using any available technology. Examples of nucleic acid sequencing technologies and methods include massively parallel sequencing, next-generation sequencing, whole genome sequencing, exome sequencing, sequencing with or without target enrichment, sequencing by synthesis (e.g., sequencing by amplification, clonal amplification, bridge amplification, sequencing with reversible terminators), sequencing by ligation, sequencing by hybridization (e.g., microarray sequencing), single-molecule sequencing, real-time sequencing, nanopore sequencing, pyrosequencing, semiconductor sequencing, sequencing by mass spectroscopy, shotgun sequencing, and Sanger sequencing. In some embodiments, sequencing is performed using massively parallel techniques on a cDNA library prepared from RNA in the sample. cDNA libraries can be synthesized as desired, for example using the mRNA-Seq Sample Preparation Kit (Illumina) following the manufacturer's instructions or with slight modifications. In some embodiments, 5-fold diluted Klenow DNA polymerase is used for the end-repair step of plasma cDNA. The QIAquick PCR Purification Kit and the QIAquick MinElute Kit (Qiagen) can be used for purifying end-repaired and adenylated products, respectively. In some embodiments, 10-fold diluted paired-end adapters are used for plasma cDNA sample, or two rounds of purification are performed for adapter-ligated products using the AMPure XP beads (Agencourt). A cDNA library can be sequenced for 75 bp in a paired-end format on a HiSeq 2000 instrument (Illumina), or using other formats or instruments.

In step 302, locations of the reads in a reference sequence are determined. For PCR-based techniques, a location can be determined, for example, by matching the color of a detected label on a probe or primer to the sequence for which the probe or primer is specific. For sequencing techniques, the location can be determined by aligning the sequence read to the reference sequence. Sequence alignment can be performed by a computer system. Any bioinformatics pipeline can be used for raw data preprocessing (such as removal of highly duplicated reads and reads of low quality), data alignment and/or data normalisation. The RNA transcript levels in the maternal blood cells, placental tissues and maternal plasma can be calculated as fragments per kilobase per millionth exonic reads (FPKM). For determining allelic ratios, data preprocessing and alignment can be performed but data normalisation is not required. Any reference sequence (for example, the hg19 reference human genome) and any algorithm can be used for alignment.

Figures 6A, 6B:
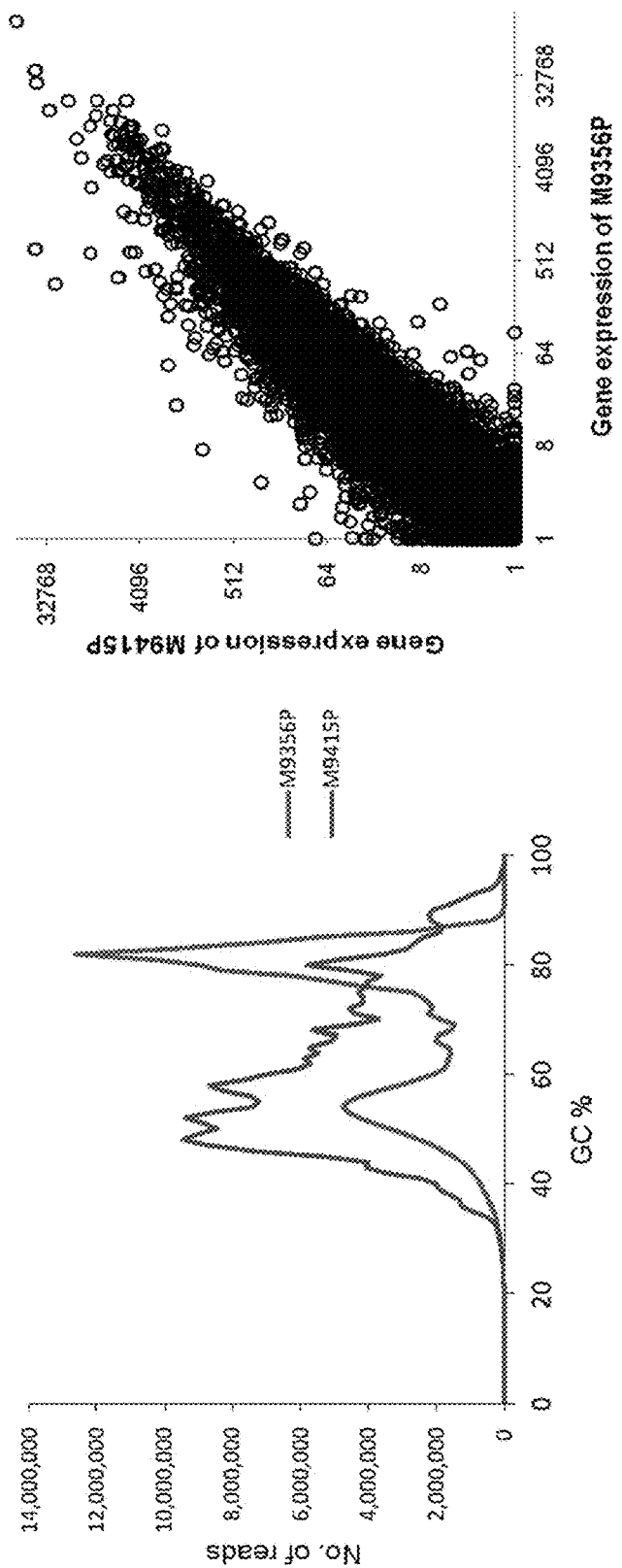
FIGS. 6A and 6B show data from sequencing the blood plasma RNA of two individuals.

In one example of carrying out steps 301 and 302, after removal of duplicated reads and rRNA reads, an average of 3 million analyzable reads were obtained for each non-pregnant female plasma sample; an average of 12 million analyzable reads were obtained for each plasma sample of pregnant women. For tissue RNA-seq, an average of 173 million and 41 million analyzable reads per sample were obtained for placenta and blood cells, respectively. The RNA-seq alignment statistics are summarized in FIGS. 4 and 5. The GC content of sequenced reads was also examined in all samples (FIG. 6A and TABLE 2).

TABLE 2

Proportion of the GC-rich sequenced reads in RNA-seq libraries.

| Sample type | Sample | Treatment | GC-rich reads (% of raw reads)[a] |
|---|---|---|---|
| Plasma | M9356P | rRNA-depletion | 49.28% |
|  | M9415P | None | 0.00% |
| Placenta | N9356 | rRNA-depletion | 0.15% |
| Blood cells | M9356W | rRNA-depletion | 0.30% |

[a]Raw reads were aligned against the de novo assembled GC-rich sequence by BLAST (NCBI).

In step 303, one or more informative loci are identified. This step can determine or make inferences about the genotypes of the female subject and fetus at loci within the genome, and compare these genotypes. A locus is considered informative if it is homozygous in a first entity for a corresponding first allele (e.g., AA), and is heterozygous in a second entity for the corresponding first allele and a corresponding second allele (e.g., AB). The first entity can be the pregnant female subject or the fetus, and the second entity is the other one of the pregnant female subject and the fetus. In other words, one individual (either the mother or fetus) is homozygous, and the other individual is heterozygous, for each informative locus.

Informative loci can be further classified according to which individual is heterozygous and the sole contributor of one allele. A locus is considered an informative maternal locus, or equivalently a maternal-specific locus, if the fetus is homozygous and the pregnant female subject is heterozygous. A locus is considered an informative fetal locus, or equivalently a fetal-specific locus, if the pregnant female subject is homozygous and the fetus is heterozygous. In step 303, the informative loci identified are all either maternal-specific or fetal-specific, because the same individual serves as the second entity for all of these loci.

An informative locus can represent a single-nucleotide polymorphism or "SNP", where the first allele and second allele differ in the identity of a single nucleotide. An informative locus can also represent a short insertion or deletion, where one or more nucleotides are inserted or deleted in one allele as compared with the other allele.

In some embodiments, the genotype of the pregnant female subject at one or more informative loci, or at each informative locus, is determined by sequencing genomic DNA obtained from maternal tissue. The maternal tissue can be maternal blood cells or any other kind of tissue. In some embodiments, the genotype of the fetus at one or more informative loci, or at each informative locus, is determined by sequencing genomic DNA obtained from fetal tissue, such as the placenta, chorionic villi, amniotic fluid. If a less invasive method is preferred, fetal DNA can also be obtained for sequencing from a maternal blood sample. The same sample used to obtain the RNA molecules for sequencing can be the source of such fetal DNA, or a different sample can be used. It will be appreciated that informative fetal loci can be identified without directly genotyping the fetus. For example, if the pregnant female subject is determined to be homozygous for a first allele at one locus, and the RNA sequencing indicate the presence of a second allele in the mixture of maternal and fetal RNA, then the fetus can be assumed to be heterozygous at this locus.

In some embodiments, the mother and fetus are both genotyped using massively parallel methods to identify informative loci. Sequencing can be performed on exome-enriched maternal blood cell and placental genomic DNA samples. Genomic DNA can be extracted from the placental tissues and maternal blood cells using the QIAamp DNA Kit and the QIAamp Blood Kit (both from Qiagen), respectively, following the manufacturer's instructions. Exome enrichment and sequencing library preparation can be performed using the TruSeq Exome Enrichment Kit (Illumina) following the manufacturer's protocol. The libraries can be sequenced for 75 bp in a PE format on a HiSeq 2000 instrument (Illumina).

In step 304, the one or more informative loci are filtered. As used herein, "filtering" means selecting certain informative loci, out of those identified in step 303, for further analysis. A "filtered" informative locus is a locus so selected. The selection can be made on the basis of one or more criteria. One such criterion is where the informative loci are located in the genome or on a reference sequence. In some embodiments, only loci located within an exon or expressed region of the reference sequence are further analyzed.

Another criterion for filtering is the number of sequence reads, out of all of those received in step 301 and aligned to the reference sequence in step 302, that align to the locus and contain each allele. In some embodiments, a filtered informative locus must have associated with it at least a first predetermined number of sequence reads containing the first allele, and/or a second predetermined number of sequence reads containing the second allele. The predetermined numbers can be 1, 2 or more, and can correspond to a desired read quality or sequencing depth. As a result of filtering, one or more filtered informative loci are identified.

In some embodiments, only informative loci representing SNPs are considered for filtering. In one example of the method, approximately one million SNPs in the NCBI dbSNP Build 135 database, all located in exons, were examined, and informative SNPs were identified out of these million using maternal and fetal genotypes. For illustration of informative SNPs, "A" was assigned as the shared allele and "B" as the maternal- or fetal-specific allele. Informative SNPs included those with a maternal-specific SNP allele, i.e. "AA" in the fetus and "AB" in the mother on a given locus, and those with a fetal-specific SNP allele, i.e. "AA" in the mother and "AB" in the fetus, on a given locus. The genotypes were called using an in-house bioinformatics pipeline. To perform filtering, only informative SNPs in which both the "A" allele and the "B" allele showed at least one read count, respectively, were included for analysis.

In steps 305 and 306, the sequence reads aligning to each filtered informative locus are counted and sorted depending on which allele they contain. For each filtered informative locus, two numbers are determined: a first number, which is the number of sequence reads aligning to the locus and containing the corresponding first allele (i.e., the shared allele); and a second number, which is the number of sequence reads aligning to the locus and containing the corresponding second allele (i.e., the maternal- or fetal-specific allele). The first number and second number can be computed as desired. The first number plus the second number for each locus provides a total number of sequence reads aligning to the locus. A ratio of the first number and the second number for a particular filtered informative locus can be referred to as an "allelic ratio".

In steps 307 and 308, the numbers of the first alleles and second alleles are summed across the filtered informative loci. In step 307, a first sum of the first numbers is calculated. The first sum represents the total number of sequence reads containing the corresponding first alleles (i.e., the shared alleles) for the filtered informative loci. In step 308, a second sum of the second numbers is calculated. The second sum represents the total number of sequence reads containing the corresponding second alleles (i.e., the maternal- or fetal-specific alleles) for the filtered informative loci. The sums can be computed as desired, using all filtered informative loci identified in step 304 or a subset thereof. In some embodiments, the sums are weighted. For example, the contributions to the sums of loci from a certain chromosome can be scaled up or down by multiplying the first numbers and second numbers for those loci by a scalar.

In step 309, a ratio of the first sum and the second sum is calculated. This ratio represents the relative numbers of sequence reads for the first alleles and second alleles, aggregated across filtered informative loci. In some embodiments, the ratio is simply calculated as the first sum divided by the second sum. Such a calculation yields the number of sequence reads for shared alleles as a multiple of sequence reads for maternal- or fetal-specific alleles. Alternatively, the ratio can be calculated as the second sum divided by the sum of the first sum and the second sum. Here the ratio provides the number of sequence reads for maternal- or fetal-specific alleles as a fraction of all sequence reads. Other methods of calculating the ratio will be apparent to the skilled artisan. The first sum and second sum, from which the ratio is calculated, can serve as proxies for the amounts of RNA (i.e., transcripts) present in the sample that originate from shared and specific alleles, for the filtered informative loci.

In step 310, the ratio calculated in step 309 is compared to a cutoff value to determine whether the fetus, mother, or pregnancy has a pregnancy-associated disorder. In various embodiments, a cutoff value can be determined from one or more samples obtained from pregnant female subjects without the pregnancy-associated disorder (i.e., control subjects) and/or determined from one or more samples obtained from pregnant female subjects with the pregnancy-associated disorder. In some embodiments, the cutoff is determined by performing the same method as described above on samples from control subjects, and examining the same or an overlapping set of filtered informative loci. A cutoff can be set at a value between expected values for pregnancies without a disorder and expected values for pregnancies with a disorder. The cutoff can be based on a statistical difference from a normal value.

In some embodiments, the ratio calculated for the pregnant female subject (as in step 309) uses filtered informative loci in a certain set of genes, and a ratio (i.e. the cutoff) is calculated for the control subjects using filtered informative loci in some or all the same genes. If the ratio calculated for the pregnant female subject is based on maternal-specific alleles, then the cutoff calculated for the control subjects can also be based on maternal-specific alleles. Similarly, the ratio and cutoff can both be based on fetal-specific alleles.

The comparison between the ratio and cutoff can be performed as desired. For example, a disorder can be diagnosed if the ratio exceeds the cutoff or falls below the cutoff, by any amount or by a certain margin. The comparison can involve calculating a difference or calculating another ratio between the ratio for the pregnant female subject and the cutoff value. In some embodiments, the comparison involves evaluating whether the relative expression levels of shared and unshared alleles for certain genes significantly differ between the pregnant female subject and the control subjects.

If desired, the method can also be used to estimate a portion of RNA in the sample that is of maternal or fetal origin. The estimate is made by multiplying the ratio calculated in step 309 by a scalar. The scalar represents a total expression level at the filtered informative loci relative to expression of the second alleles in the heterozygous individual.

The following example illustrates application of the scalar. If the second alleles counted in the method are fetal-specific, then the ratio calculated in step 309 can provide the number of sequence reads for fetal-specific alleles as a fraction of all sequence reads for the filtered informative loci. Of the sequence reads containing the shared allele, some are contributed by the mother and some are contributed by the fetus. If the relative expression levels of the fetal-specific and shared alleles in the fetus are known, or can be estimated, then the ratio can be scaled to obtain an estimate of the fractional fetal contribution to all sequence reads for the filtered informative loci.

In some embodiments, the fetal and shared alleles are expressed symmetrically at most loci and the scalar is assumed to be about two In other embodiments, the scalar departs from two and takes into account asymmetric gene expression[24]. The fractional maternal contribution to sequence reads is then one minus the fractional fetal contribution. Similar calculations can be made when the second alleles at the filtered informative loci are maternal-specific.

B. Examples

1. Correlation of Allelic Ratios and Plasma Concentrations

The expression profile of a maternal plasma sample (gestational age 37 2/7) was analyzed and compared with the corresponding placenta and maternal blood cells for a pregnant woman. Massively parallel sequencing of RNA was performed for each of these samples using the Illumina HiSeq 2000 instrument. The placenta and the maternal blood cells were genotyped using exome sequencing by massively parallel sequencing. We examined approximately one million SNPs in the NCBI dbSNP Build 135 database that were located in the exons, and sorted for informative SNPs where the mother is homozygous (genotype AA) and the fetus is heterozygous (genotype AB). Thus, the A allele would be the allele shared between the mother and the fetus and the B allele is fetal-specific.

Figure 7:
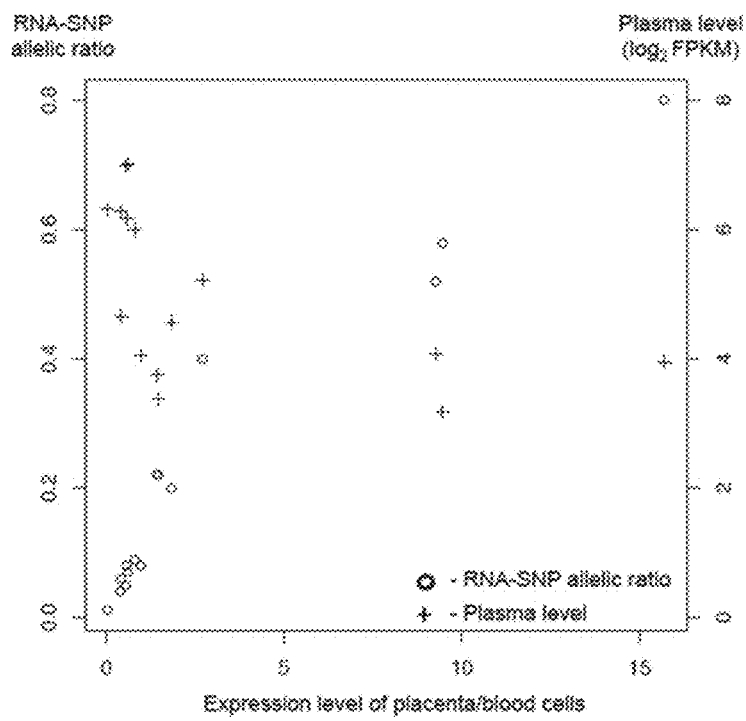
FIG. 7 shows the RNA-SNP allelic ratios and the total plasma concentrations of different RNA transcripts in the maternal plasma plotted against the relative tissue expression levels (placenta/blood cells).

The RNA-SNP allelic ratios and the total plasma concentrations of different RNA transcripts in the maternal plasma are plotted against the relative tissue expression levels (placenta/blood cells) (FIG. 7). We can observe that the RNA-SNP allelic ratio in the plasma correlates well with the relative tissue expression level (Spearman R=0.9731679, P=1.126e-09) However, the total plasma level did not correlate with the tissue expression (Spearman R=−0.7285714, P=0.002927).

Figure 8:
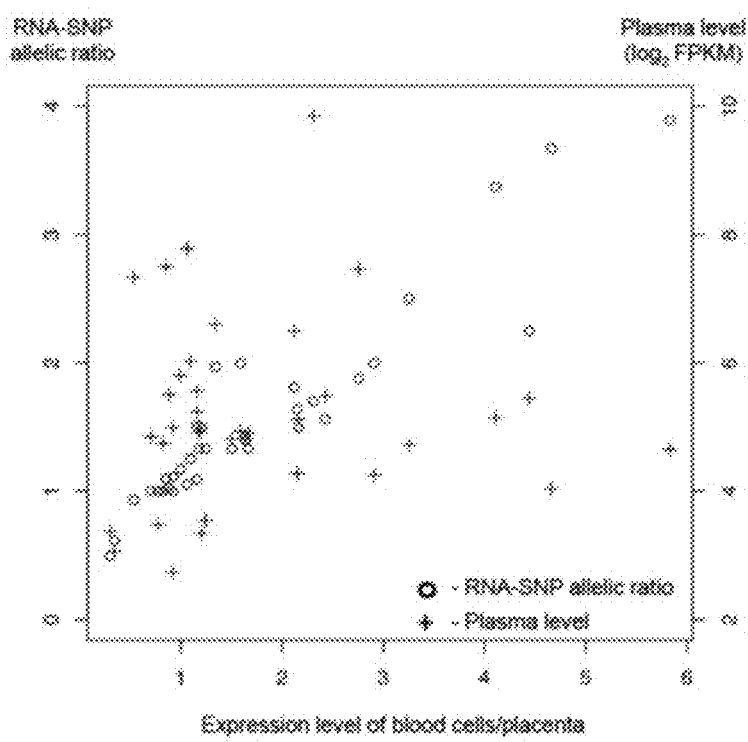
FIG. 8 shows the RNA-SNP allelic ratios and total plasma levels of different genes containing informative SNPs plotted against the relative tissue expression level (blood cells/placenta).

In addition to the analysis of the fetal expression, this method can also be used for the profiling of the maternal expression. In this scenario, informative SNPs that the mother is heterozygous (genotype AB) and the fetus is homozygous (genotype AA) can be used. The RNA-SNP allelic ratio can then be calculated as the maternal-specific allelic count divided by the count of the shared allele. In FIG. 8, the RNA-SNP allelic ratios and total plasma levels of different genes containing informative SNPs are plotted against the relative tissue expression level (blood cells/placenta). We can observed a good positive relationship between the tissue expression level with the RNA-SNP allelic ratio in the maternal plasma (Spearman R=0.9386, P<2.2e-16) but not the total plasma transcript levels (Spearman R=0.0574, P=0.7431).

The RNA transcripts, their RNA-SNP allelic ratios and their plasma levels are tabulated in FIG. 9 and FIG. 10.

Figure 11A:
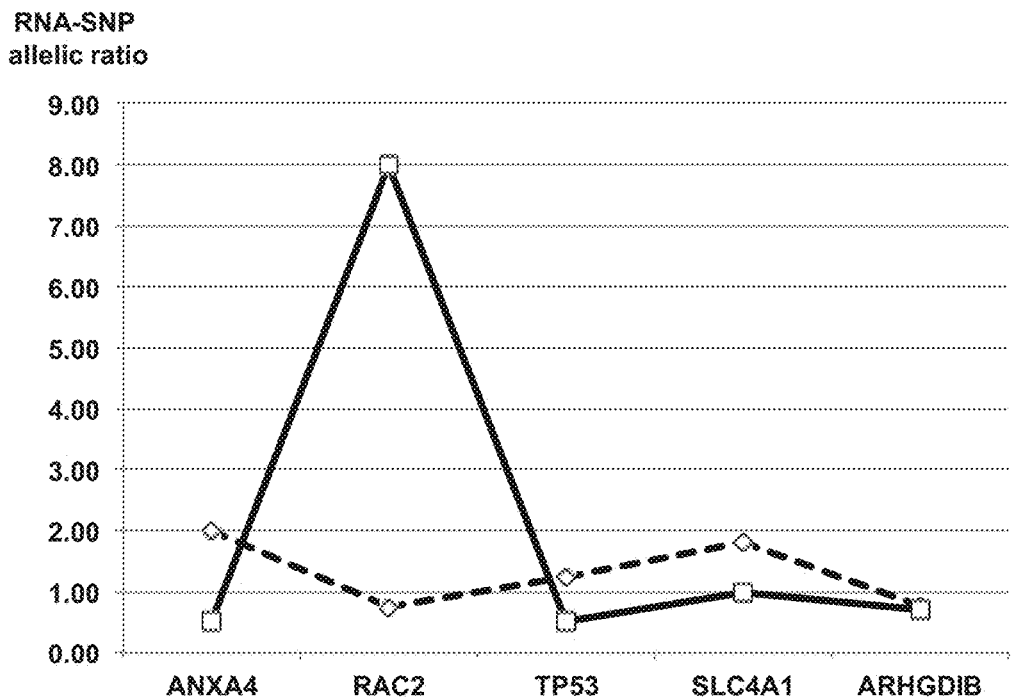
FIGS. 11A and 11B show data for maternal-specific SNP alleles in pre-eclamptic and control subjects.
Figure 11B:
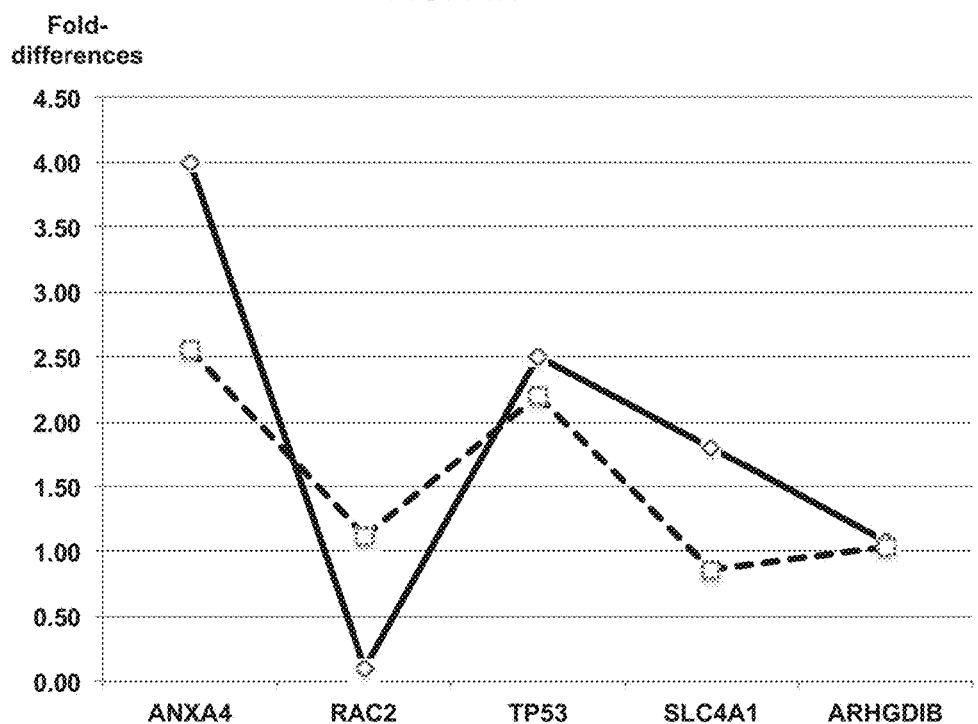
Figure 12A:
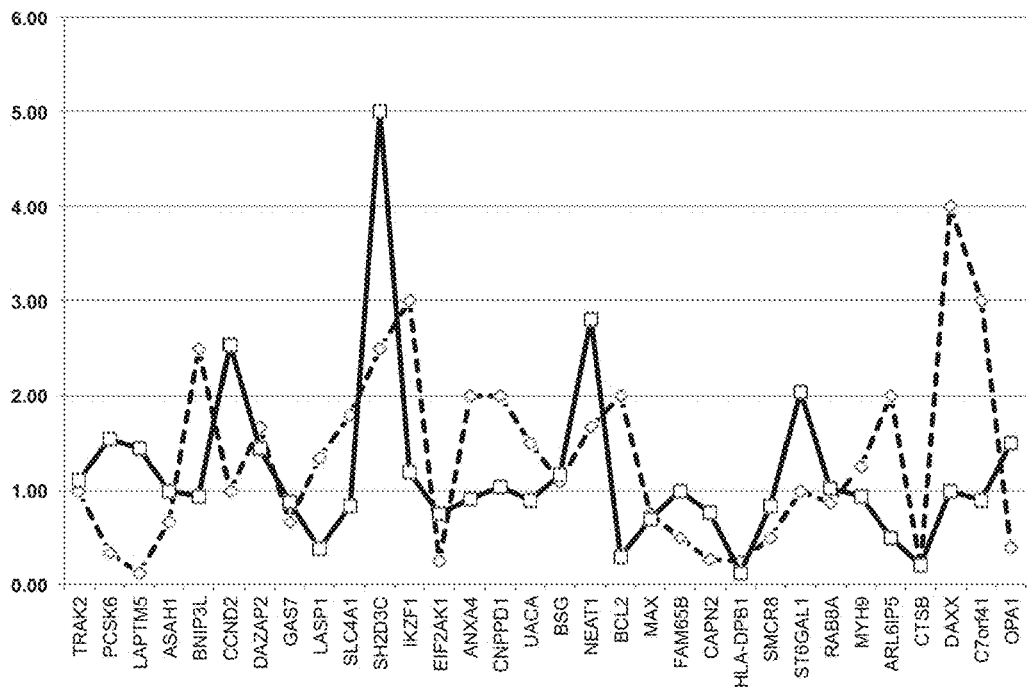
FIGS. 12A and 12B show data for maternal-specific SNP alleles in pre-eclamptic and control subjects.
Figure 12B:
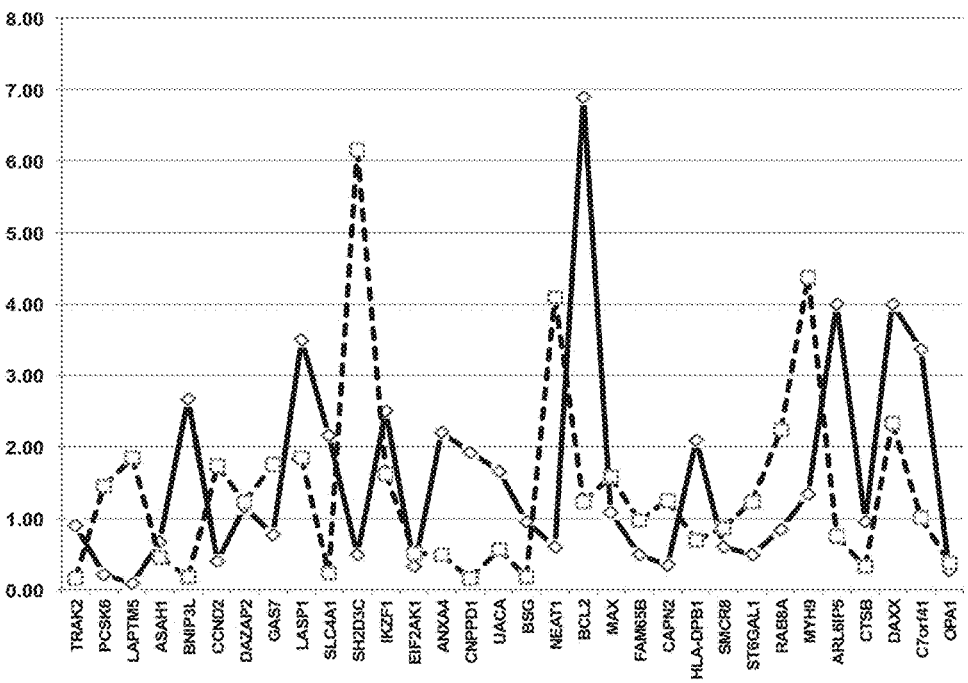
Figure 14:
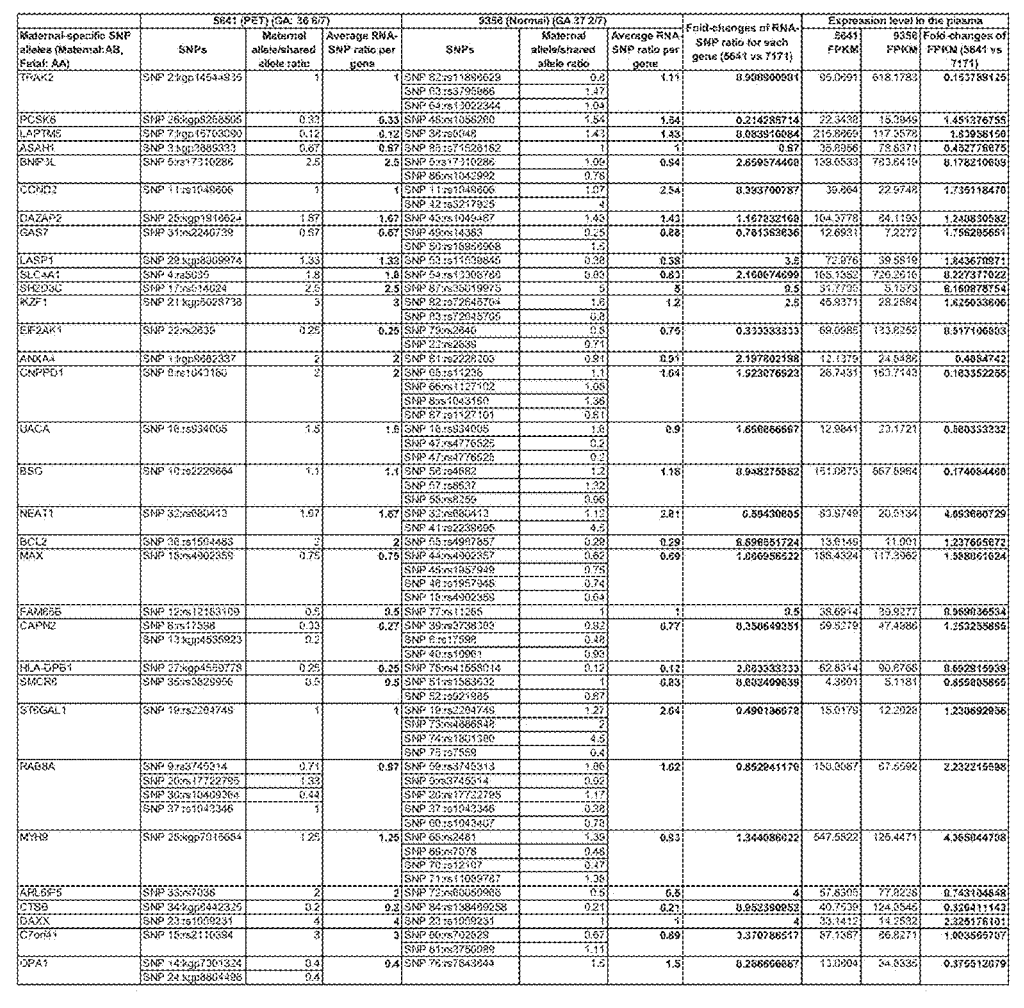

2. Comparison of Maternal Plasma RNA-SNP Allelic Ratio for Preeclampsia and Control Pregnancy Cases For the cases of two pregnant female subjects, an average number of 117,901,334 raw fragments were obtained (TABLE 3A). The RNA-SNP allelic ratio of a subset of circulating transcripts bearing maternal-specific SNP alleles was compared between a third-trimester late-onset preeclampsia (PET) case, 5641, and its gestational age-matched control case, 7171. As shown in FIG. 11A, the RNA-SNP allelic ratios of these transcripts portrayed a different profile in the PET and the control cases. Importantly, the RNA-SNP allelic ratio profile is distinct from the plasma transcript level profile, as shown in FIG. 11B. This suggests that the maternal plasma RNA-SNP allelic ratio analysis could be utilized as another metric to better distinguish PET cases from a normal pregnancy cases. The number of informative transcripts could be further increased with an increased number of informative SNPs, exemplified by the comparison between the PET case, 5641, and another normal pregnancy control case, 9356 (FIGS. 12A and 12B). The RNA-SNP allelic ratios and the plasma level of the RNA transcripts shown in FIGS. 11A, 11B, 12A, and 12B are tabulated in FIG. 13 and FIG. 14.

TABLE 3A

Summary of RNA-seq read alignment results.

| Sample type | Sample | Raw reads | Preprocessed[a] reads | (%)[b] | Mappable reads[c] | (%)[d] |
|---|---|---|---|---|---|---|
| Maternal plasma | 5641 (Preeclampsia) | 119,902,178 | 30,106,800 | 25.11% | 4,001,376 | 13.29% |
| Maternal plasma | 7171 (Control) | 115,900,490 | 29,160,920 | 25.16% | 1,397,345 | 4.79% |

[a]Retained reads after removal of highly repetitive reads.
[b]% of the raw reads.
[c]See Supplemental Data Table 2B for detailed breakdown.
[d]% of the preprocessed reads.

TABLE 3B

Summary of RNA-seq read alignment results

| Sample type | Sample | Filtered reads[a] | Analyzable reads[b] | Exon (%) | Intron (%) | Intergenic region (%)[c] |
|---|---|---|---|---|---|---|
| Maternal plasma | 5641 (Preeclampsia) | 2,579,163 | 1,422,213 | 44.87% | 12.32% | 42.80% |
| Maternal plasma | 7171 (Control) | 790,735 | 606,610 | 37.69% | 16.09% | 46.22% |

[a]Filtered reads are mostly the nuclear and mitochondrial rRNAs and tRNAs.
[b]Analyzable reads = total mappable reads − filtered reads.
[c]% of reads that aligned to regions outside exons and introns of the reference genes.

III. Method of Determining Fetal or Maternal RNA Contribution

A. Method

Figure 15:
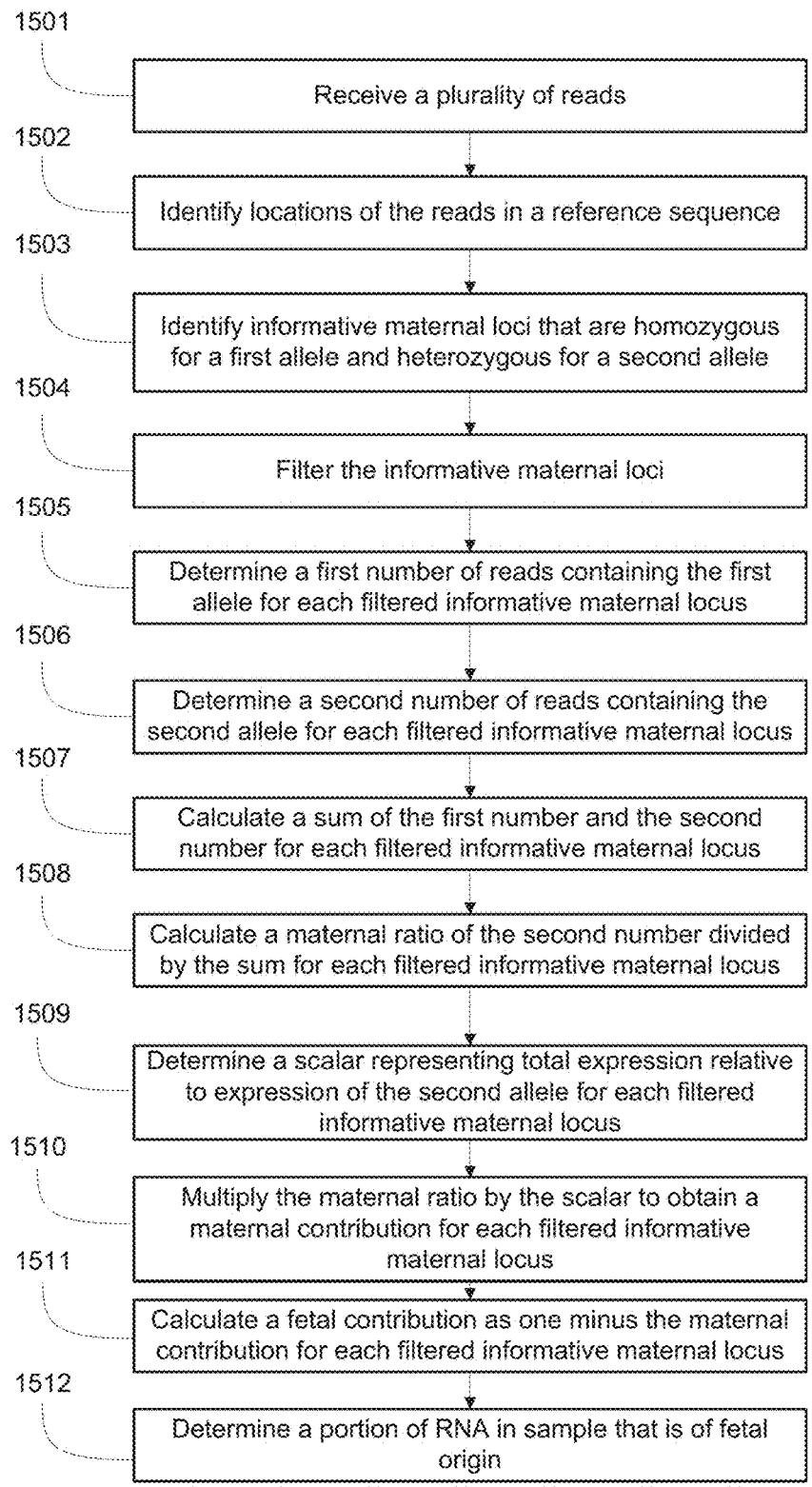
FIG. 15 is a flowchart for methods of determining, in a sample from a female subject pregnant with a fetus, a portion of RNA that is of fetal origin

A method 1500 is shown in FIG. 15 for determining, in a sample from a female subject pregnant with a fetus, a portion of RNA that is of fetal origin. The sample can be obtained and prepared as discussed above for method 300.

In step 1501, a plurality of sequence reads are received. In step 1502, the sequence reads are aligned to a reference sequence. These steps can be performed as described above for steps 301 and 302.

In step 1503, one or more informative maternal loci are identified. Each informative maternal locus is homozygous in the fetus for a corresponding first allele and heterozygous in the pregnant female subject for the corresponding first allele and a corresponding second allele. The first allele is thus shared between the mother and fetus, and the second allele is maternal-specific. The informative maternal loci can be identified as described above for step 303.

In step 1504, the informative maternal loci are filtered, as in step 304, and one or more filtered informative maternal loci are identified. Sequence reads are then manipulated on the level of individual filtered informative maternal loci in steps 1505-1511. In steps 1505 and 1506, a first number and a second number are determined for each filtered informative maternal locus. The first number is determined in step 1505 as the number of sequence reads aligning to the locus and containing the corresponding first allele. The second number is determined in step 1506 as the number of sequence reads aligning to the locus and containing the corresponding second allele. Steps 1505 and 1506 can be performed similarly to steps 305 and 306, discussed above.

In step 1507, a sum of the first number and the second number is calculated for each informative maternal locus. The sum can be equivalent to the total number of sequence reads aligning to the locus. In step 1508, a maternal ratio is calculated by dividing the second number by the sum. The maternal ratio provides the fraction of all sequence reads aligning to the particular locus that contain the second (maternal-specific) allele.

In step 1509, a scalar is determined. The scalar represents a total expression level at the filtered informative maternal locus relative to expression of the corresponding second allele in the pregnant female subject. In some embodiments, where expression of the two alleles in the pregnant female subject is known or assumed to be symmetrical, the scalar is about two. In other embodiments, the scalar can depart from two and take into account asymmetrical gene expression. As most loci express symmetrically, the assumption of symmetry is valid.

In step 1510, the maternal ratio is multiplied by the scalar to obtain a maternal contribution. The maternal contribution represents, at the filtered informative maternal locus, the fraction of sequence reads (or, by extension, the fraction of RNA in the sample) that is contributed by the mother. One minus the maternal contribution is the fetal contribution, or the fraction of sequence reads contributed by the fetus. In step 1511, the fetal contribution is calculated for the filtered informative maternal locus.

In step 1512, a portion of RNA in the sample that is of fetal origin is determined. The portion is the average of the fetal contributions for the filtered informative maternal loci. In some embodiments, this average is weighted, for example by the sums calculated for the filtered informative maternal loci. By calculating a weighted average, the portion determined in step 1512 can reflect the relative expression levels of different loci or genes in the sample.

The portion of RNA in the sample that is of fetal origin can be calculated for one filtered informative maternal locus, many such loci, or all such loci for which sequencing data are obtained. It will be appreciated that this portion reflects the circulating transcriptome in the particular pregnant female subject at the time the sample was acquired. If samples are obtained from the subject at different times over the course of the pregnancy, the set of filtered informative maternal loci identified in method 1500 may vary from one sample to the next, as may the portions of fetal-originating RNA determined at these loci. The portion of RNA in a sample that is of fetal origin can also vary from one subject to the next, even when controlling for gestational stage or other factors, and can differ between a subject having a pregnancy-associated disorder and a healthy subject. Accordingly, the portion can be compared to a cutoff-value to diagnose such a disorder.

In some embodiments, the cutoff value is determined by performing method 1500 using samples from one or more healthy subjects. In some embodiments, a diagnosis is made if the portion exceeds the cutoff or falls below the cutoff, by any amount or by a certain margin. The comparison can involve calculating a difference or calculating a ratio between the portion of fetal-originating RNA in the pregnant female subject and the cutoff value. In some embodiments, the comparison involves evaluating whether the portion of fetal-originating RNA in the pregnant female subject differs significantly from what is seen in healthy pregnant women at similar gestational periods.

The portion of RNA in the sample that is of fetal origin can also be determined by examining informative fetal loci. At each informative fetal locus, this portion can be estimated by first calculating a fetal ratio, which is the number of sequence reads containing the second (fetal-specific) allele divided by the total number of sequence reads. The fetal contribution is then the fetal ratio multiplied by a scalar representing the relative expression levels of the two alleles in the fetus. Accordingly, a variation of method 1500 can be performed by identifying informative fetal loci, filtering these loci, calculating a fetal contribution for each filtered locus, and averaging the fetal contributions for the filtered loci. If desired, the fetal-originating portion of RNA determined by method 1500 can be augmented by averaging the fetal contributions calculated for filtered informative maternal loci with fetal contributions calculated for filtered informative fetal loci. The averages calculated here can be weighted, to reflect variation in the number of sequence reads at different loci, to give more weight to maternal- or fetal-specific loci, or otherwise as desired.

B. Examples

Figure 18A:
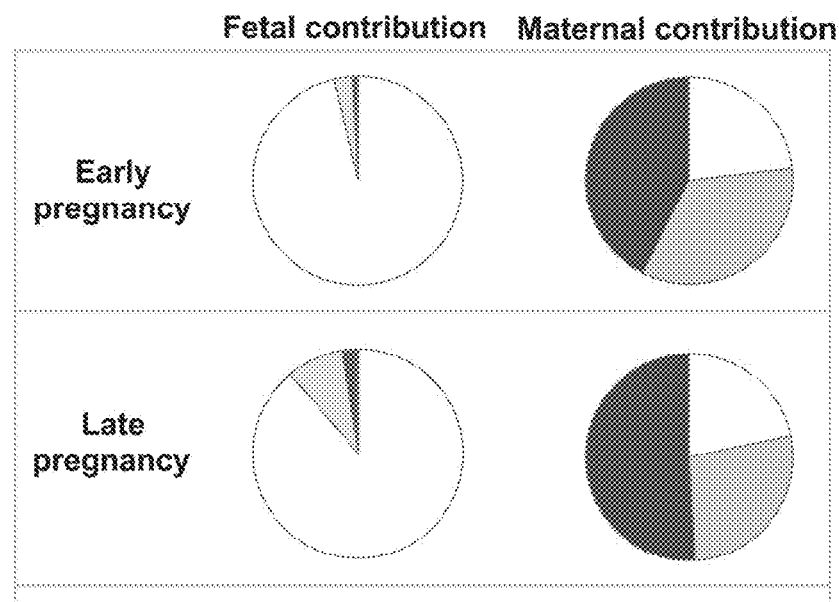
FIGS. 18A and 18B show fetal and maternal contributions in the maternal plasma transcriptome.

1. Identification and Estimation of Fetal- and Maternal-Derived Transcript in Maternal Plasma Informative genes, defined as genes with at least one informative SNP, were first identified based on the genotyping data. In the two early pregnancy cases, a total number of 6,714 and 6,753 informative genes were available to examine the relative proportions of fetal and maternal contributions, respectively (FIGS. 16 and 17). In the two late pregnancy cases, a total number of 7,788 and 7,761 informative genes were available to examine the relative proportions of fetal and maternal contributions, respectively. To measure the relative proportion of fetal contribution in the maternal plasma, we sorted for RNA transcripts where the fetal-specific alleles were covered by at least one RNA-seq read in the maternal plasma samples. The relative proportions of such fetal-derived transcripts were 3.70% and 11.28% during early and late gestations, respectively. Using a similar approach, the relative proportions of maternal contribution in the circulation, examined using the maternal-specific SNP alleles, was estimated to be 76.90% and 78.32% during early and late gestations, respectively (FIG. 18A).

2. Comparison of RNA-SNP Fractional Fetal and Maternal Contribution for PET and Control Pregnancy Cases We have examined the fractional fetal and maternal contribution for GNAS transcript, which was detected in both the PET case, 5641, and its gestational age-matched control case, 7171. In the GNAS transcript, there was an informative SNP site comprising fetal-specific SNP allele at locus rs7121 in case 5641; on the same SNP site in case 7171, there was a maternal-specific SNP allele. The fractional fetal and maternal contributions for this SNP site in case 5641 were calculated to be 0.09 and 0.91, respectively. On the other hand, the fractional fetal and maternal contributions for the same SNP site in case 7171 were 0.08 and 0.92, respectively (FIG. 19). Compared to the control case 7171, there was a 12.5% increase in the fractional fetal contribution and a 1.09% decrease in the fractional maternal contribution in this transcript. Interestingly, a 21% increase in FPKM was detected for this transcript in case 5641 compared to 7171.

IV. Method of Designating a Genomic Locus as a Maternal or Fetal Marker

A. Method

Figure 20:
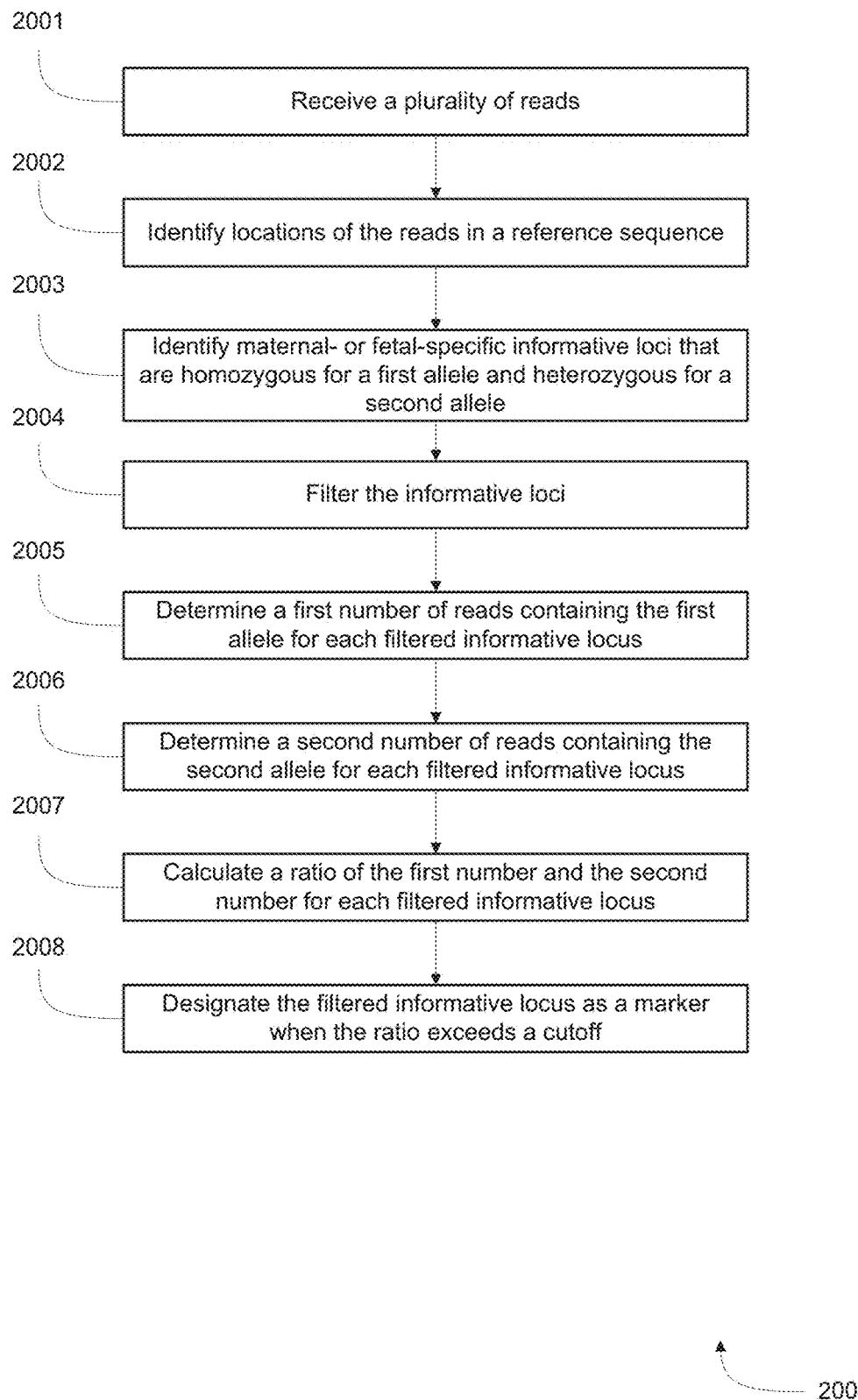
FIG. 20 is a flowchart for methods of designating a genomic locus as a maternal or fetal marker.

A method 2000 of designating a genomic locus as a maternal or fetal marker is shown in FIG. 20. The method involves analyzing a sample from a female subject pregnant with a fetus. The sample can be of maternal blood plasma and contains a mixture of maternal- and fetal-derived RNA molecules. The sample can be obtained and prepared as discussed above for method 300.

In step 2001, a plurality of sequence reads are received. In step 2002, the sequence reads are aligned to a reference sequence. These steps can be performed as described above for steps 301 and 302.

In step 2003, one or more informative loci are identified. Each locus is homozygous in a first entity for a corresponding first allele and heterozygous in a second entity for the corresponding first allele and a corresponding second allele. The first entity is the pregnant female subject or the fetus, and the second entity is the other one of the pregnant female subject and the fetus. The informative loci can be identified as described above for step 303.

In step 2004, the informative loci are filtered, as in step 304, and one or more filtered informative loci are identified. In some embodiments, only informative loci representing SNPs are considered for filtering. In one example of the method, filtered informative loci included informative SNPs with at least one sequence read for the "A" allele and one sequence read for the "B" allele in the maternal plasma.

Sequence reads are then manipulated on the level of individual filtered informative loci in steps 2005-2008. In steps 2005 and 2006, a first number and a second number are determined for each filtered informative locus. The first number is determined in step 2005 as the number of sequence reads aligning to the locus and containing the corresponding first allele. The second number is determined in step 2006 as the number of sequence reads aligning to the locus and containing the corresponding second allele. Steps 2005 and 2006 can be performed similarly to steps 305 and 306, discussed above.

In step 2007, a ratio of the first number and the second number is calculated for each filtered informative locus. This ratio represents the relative abundances of sequence reads (and, by extension, transcripts in the sample) containing the first allele and the second allele. In some embodiments, the ratio is simply calculated as the first number divided by the second number. Such a calculation yields the number of sequence reads for the shared allele as a multiple of sequence reads for the maternal- or fetal-specific allele. This ratio, or its reciprocal, can be considered an allelic ratio, and for SNP loci, an RNA-SNP allelic ratio.

In some embodiments, for informative SNPs that include maternal-specific SNP alleles, the RNA-SNP allelic ratio for each SNP is calculated as maternal-specific allele:shared allele. On the other hand, for informative SNPs that include fetal-specific SNP alleles, the RNA-SNP allelic ratio can be calculated as fetal-specific allele:shared allele. Unlike gene expression analysis, in which data normalisation is a prerequisite, RNA-SNP allelic ratio analysis does not require data normalisation and less bias is introduced. For transcripts that contain more than one informative SNP, an RNA-SNP allelic ratio can be calculated for each informative SNP site and an average RNA-SNP allelic ratio per transcript can be computed.

In step 2007, the ratio can alternatively be calculated as the second number divided by the sum of the first number and the second number. Here the ratio provides the number of sequence reads for the maternal- or fetal-specific allele as a fraction of all sequence reads at the locus. In terms of "A" and "B" alleles, the ratio can be expressed as $B$-allele ratio=$B$-allele count/($A$-allele count+$B$-allele count)

Theoretically, for a plasma transcript that is contributed solely by the fetus or by the mother, the B-allele ratio should be 0.5, assuming no allele-specific expression. Other methods of calculating the ratio will be apparent to the skilled artisan.

In step 2008, the filtered informative locus is designated as a marker when the ratio exceeds a cutoff. In some embodiments, the cutoff is from about 0.2 to about 0.5. In some embodiments the cutoff is 0.4. In one example of the method, a B-allele ratio cutoff was defined as ≥0.4 for an RNA transcript with high fetal or maternal contribution. This cutoff took into consideration the Poisson distribution and random sampling of RNA-seq reads. In some embodiments, the contribution of the "B" allele is said to be high when the ratio exceeds the cutoff.

A high allelic ratio at a particular informative locus can indicate that (i) the second or "B" allele is more highly expressed in the heterozygous individual than the "A" allele (i.e., the allele is expressed asymmetrically), (ii) a greater share of all RNA aligning to the locus in the maternal plasma is contributed by the heterozygous individual, or both (i) and (ii). A high allelic ratio can also indicate a pregnancy-associated disorder if the gene associated with the informative locus is being pathologically overexpressed. Accordingly, some embodiments of the method also include diagnosing a pregnancy-associated disorder based upon whether a filtered informative locus is designated as a marker for the second entity (i.e., the heterozygous individual). In making such a diagnosis, the cutoff used for comparison to the allelic ratio can be based on transcript levels in plasma samples obtained from healthy pregnant subjects.

In some embodiments, method 2000 can also be used to estimate a portion of RNA in the sample, at a particular filtered informative locus, that is of maternal or fetal origin. The estimate is made by multiplying the ratio calculated in step 2007 by a scalar. The scalar represents a total expression level at the locus relative to expression of the second allele in the heterozygous individual.

To illustrate, if the second ("B") allele counted in the method is fetal-specific, then the B-allele ratio, calculated as above, represents the number of sequence reads for this allele as a fraction of all sequence reads for the filtered informative locus. Of the sequence reads containing the shared ("A") allele, some are contributed by the mother and some are contributed by the fetus. If the relative expression levels of the fetal-specific and shared alleles in the fetus are known, or can be estimated, then the B-allele ratio can be scaled to obtain an estimate of the fractional fetal contribution to all sequence reads for the locus. If the "A" and "B" alleles are expressed equally in the fetus, then the scalar is about two. The fractional maternal contribution to sequence reads at the locus is then one minus the fractional fetal contribution. Similar calculations can be made when the "B" allele at the filtered informative locus is maternal-specific.

B. Example

High Fetal and Maternal Contributions

Using a B-allele cutoff of 0.4 as described above, 0.91% of the circulating transcripts were found to show high contribution by the fetus during early gestation (i.e. the first and second trimesters). This percentage increased to 2.52% during late gestation (i.e. the third trimester). On the other hand, 42.58% and 50.98% showed high contribution by the mother during early and late gestations, respectively (FIGS. 16, 17, and 18A).

V. Use of a Genes for Diagnosing Pregnancy-Associated Disorders

A. Pregnancy-Associated Genes

A method of identifying pregnancy-associated genes is also provided. The method includes receiving a plurality of first sequence reads and plurality of second sequence reads. The first sequence reads result from sequencing RNA molecules obtained from a blood plasma sample of a pregnant woman. The second sequence reads result from sequencing RNA molecules obtained from a blood plasma sample of a non-pregnant woman. The first sequence reads and the second sequence reads are aligned with a reference sequence, and a set of candidate genes is designated.

According to the method, sequence reads are then used to determine expression levels for each candidate gene in the samples from the pregnant woman and the non-pregnant woman. Specifically, for each candidate gene, a first number of transcripts corresponding to the candidate gene is determined using the first sequence reads; and a second number of transcripts corresponding to the candidate gene is determined using the second sequence reads. The first number of transcripts and the second number of transcripts can be normalized. A transcript ratio for the candidate gene is then calculated, where the transcript ratio includes the first number of transcripts divided by the second number of transcripts. The transcript ratio is then compared with a cutoff. The candidate gene is identified as a pregnancy-associated gene if the transcript ratio exceeds the cutoff.

In some embodiments of the method, normalizing the first number of transcripts corresponds to scaling the first number of transcripts by the total number of first sequence reads. Similarly, normalizing the second number of transcripts can correspond to scaling the second number of transcripts by the total number of second sequence reads. In other embodiments, normalizing the first number of transcripts for each candidate gene corresponds to scaling the first number of transcripts for the candidate gene by the total number of first transcripts for all candidate genes. Normalizing the second number of transcripts for each candidate gene can correspond to scaling the second number of transcripts for the candidate gene by the total number of second transcripts for all candidate genes.

The method generally identifies genes as pregnancy-associated if they are expressed at higher levels in a pregnant woman as compared with a non-pregnant woman, all else being equal. The pregnant and non-pregnant women can be the same individual; that is, samples obtained from the individual before and after giving birth can be the sources of the first sequence reads and the second sequence reads, respectively.

Figure 18B:
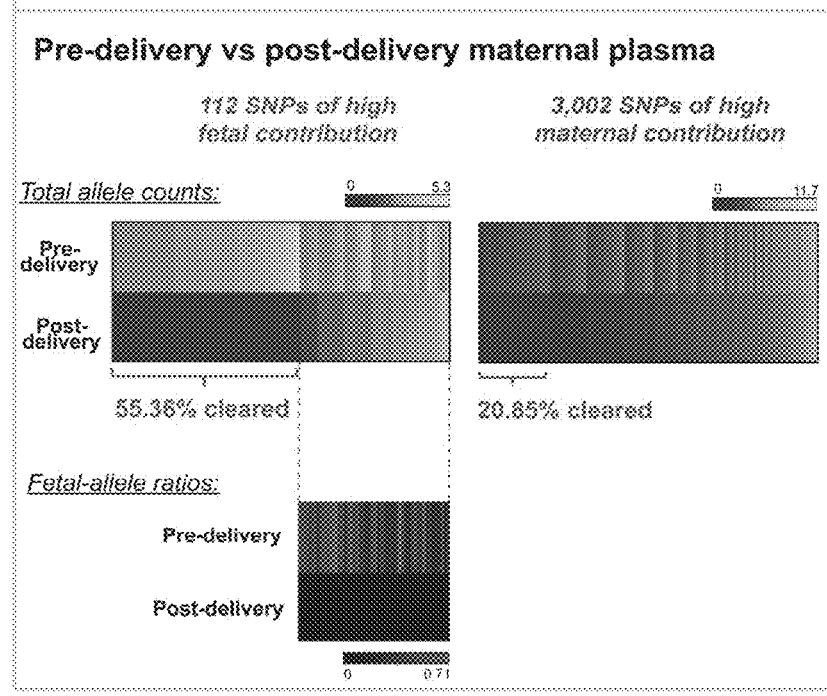
Figure 22:
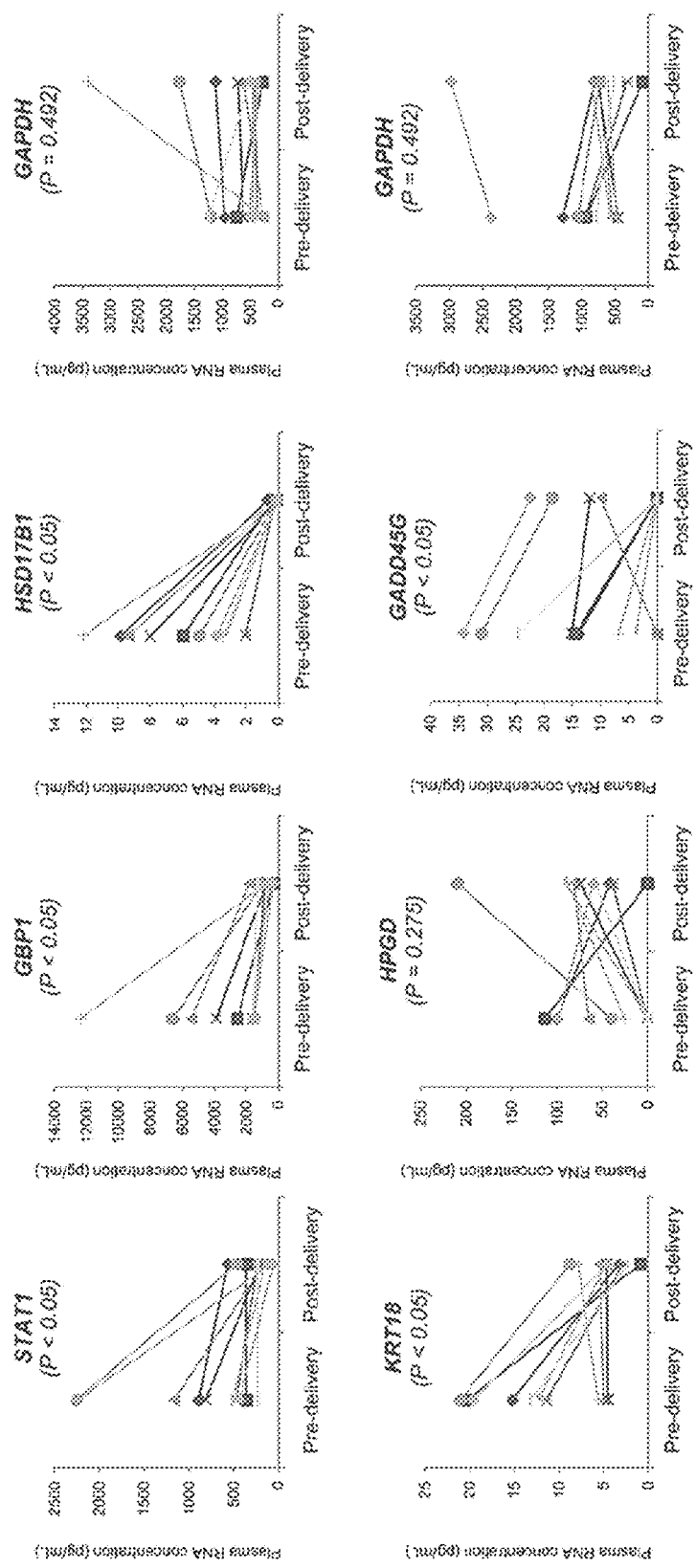
FIG. 22 shows lower expression levels of pregnancy-associated genes in subjects post-delivery as compared with pre-delivery.

We have shown that a subset of circulating RNA transcripts bearing fetal-specific alleles completely disappeared from the maternal plasma after delivery (FIG. 18B). These transcripts were considered to be fetal-specific in maternal plasma. On the other hand, a portion of maternal-specific alleles was also undetectable after delivery. Thus, we explored genes that showed up-regulation during pregnancy, termed pregnancy-associated genes, by directly comparing their representation in the pre- and post-delivery maternal plasma. We defined pregnancy-associated genes as those that were detected in the pre-delivery plasma of the third-trimester pregnant women, which their post-partum plasma level was decreased by ≥2-fold in both cases. By using a bioinformatics algorithm for data normalization and differential gene expression analysis, we compiled a list of 131 pregnancy-associated genes (FIG. 21). Among these genes, 15 were previously reported to be pregnancy-specific in maternal plasma[1,2,4,5,9,10,12]. Using one-step real-time RT-PCR, we have further validated the pregnancy-association of five newly-identified transcripts, which were abundant in pre-delivery maternal plasma, i.e. STAT1, GBP1 and HSD17B1 in 10 additional plasma samples from third-trimester pregnant women, as well as KRT18 and GADD45G in 10 plasma samples from another cohort of third-trimester pregnant women (FIG. 22).

Figure 23:
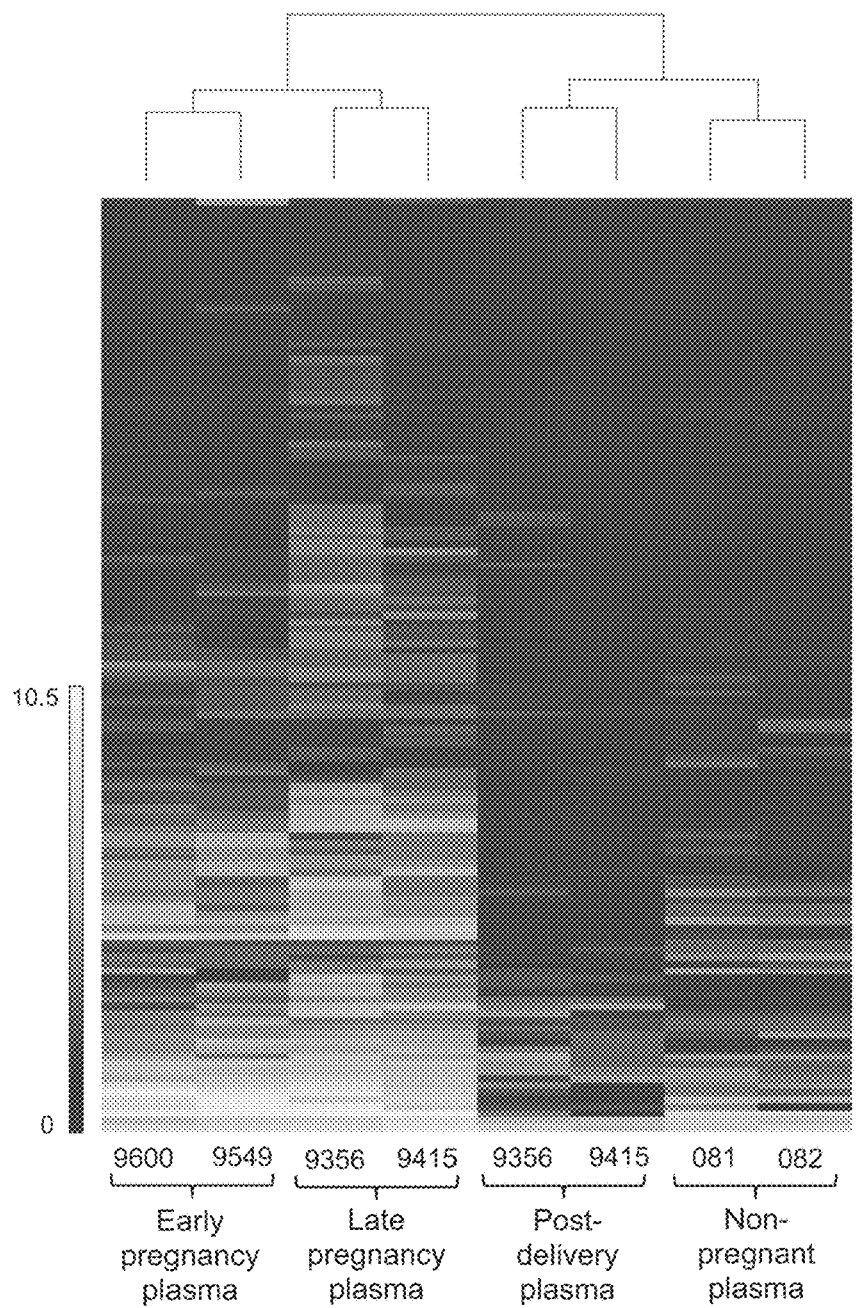
FIG. 23 shows hierarchical clustering of plasma samples using the 131 pregnancy-associated genes.

To assess the association of these 131 genes with pregnancy, hierarchical clustering was performed for all the plasma samples. A clear separation was observed between the plasma samples from pregnant women (i.e. early and late pregnancy) and those not associated with on-going pregnancy (i.e. non-pregnant controls and post-delivery) (FIG. 23).

Figure 24B:
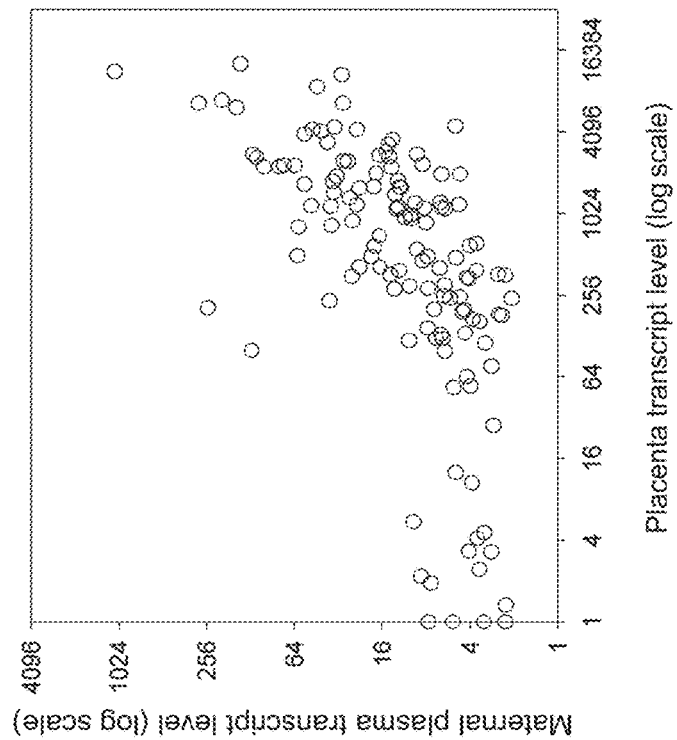
FIGS. 24A and 24B show expression levels of 131 pregnancy-associated genes in the placenta, maternal bloods cells and maternal plasma.
Figure 24A:
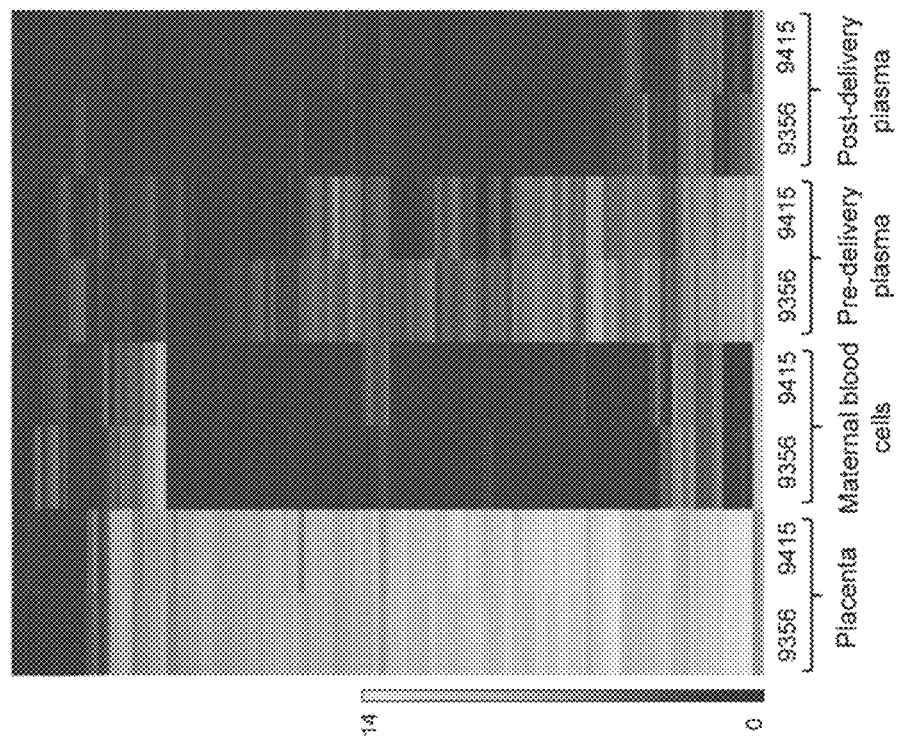

Interestingly, when the expression patterns of these 131 genes were compared between the plasma samples of the two late pregnancy cases and their corresponding placenta and maternal blood cells, a closer resemblance was observed between the placenta and the pre-delivery plasma samples, and between the maternal blood cells and the post-partum plasma samples (FIG. 24A). This observation supports the thesis that most pregnancy-associated genes are preferentially expressed in the placenta than in the maternal blood cells. Furthermore, the expression levels of these pregnancy-associated transcripts in the placentas and maternal plasma were positively correlated (P<0.05, Spearman correlation) (FIG. 24B).

B. Differential Gene Expression in Placenta and Maternal Blood

Figure 25:
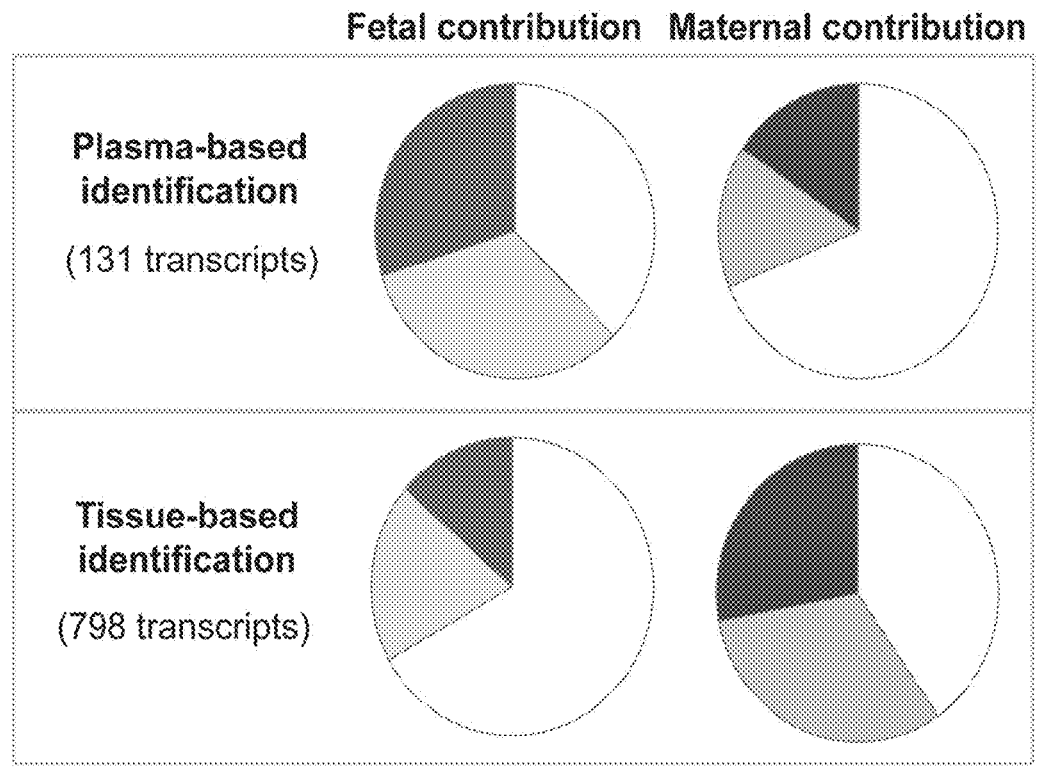
FIG. 25 compares fetal and maternal contributions to RNA in the plasma for genes identified with plasma- and tissue-based methods.

While we were able to catalog a panel of pregnancy-associated genes through direct examination of the pre- and post-delivery maternal plasma samples, we have also mined the placental and blood cell RNA-seq data for comparison purposes. Assuming that pregnancy-associated genes should be those expressed at a high level in the placenta and at a low level in the maternal blood cells as reported before[10,15], we arbitrarily set a 20-fold difference as a minimum cut-off for the tissue-based analysis. This tissue-based analysis yielded a total of 798 potential candidate genes, in which the proportions of fetal and maternal contributions in the maternal plasma were calculated. A relatively high proportion of genes with predominant fetal contribution was identified (FIG. 25) when compared to that of the full transcriptome (FIG. 18A). However, the plasma-based strategy outperformed the tissue-based strategy in being able to identify a higher proportion of genes with predominant fetal contribution (FIG. 25).

C. Genes Associated with Disease or Disorder

Also provided herein is a method of identifying genes associated with a pregnancy-associated disorder. The method includes receiving a plurality of first sequence reads and plurality of second sequence reads. The first sequence reads result from sequencing RNA molecules obtained from a blood plasma sample of a healthy pregnant woman. The second sequence reads result from sequencing RNA molecules obtained from a blood plasma sample of a pregnant woman suffering from a pregnancy-associated disorder, or carrying a fetus suffering from a pregnancy-associated disorder. The first sequence reads and the second sequence reads are aligned with a reference sequence, and a set of candidate genes is designated.

According to the method, sequence reads are then used to determine expression levels for each candidate gene in the samples for the two pregnant women. Specifically, for each candidate gene, a first number of transcripts corresponding to the candidate gene is determined using the first sequence reads, and a second number of transcripts corresponding to the candidate gene is determined using the second sequence reads. The first number of transcripts and the second number of transcripts can be normalized. A transcript ratio for the candidate gene is then calculated, where the transcript ratio includes the first number of transcripts divided by the second number of transcripts. The transcript ratio is then compared with a reference value. The candidate gene is identified as associated with the disorder if the transcript ratio deviates from the reference value.

In some embodiments of the method, normalizing the first number of transcripts corresponds to scaling the first number of transcripts by the total number of first sequence reads. Similarly, normalizing the second number of transcripts can correspond to scaling the second number of transcripts by the total number of second sequence reads. In other embodiments, normalizing the first number of transcripts for each candidate gene corresponds to scaling the first number of transcripts for the candidate gene by the total number of first transcripts for all candidate genes. Normalizing the second number of transcripts for each candidate gene can correspond to scaling the second number of transcripts for the candidate gene by the total number of second transcripts for all candidate genes.

According to the method of identifying genes associated with a pregnancy-associated disorder, in some embodiments, the reference value is 1. In some embodiments, the transcript ratio deviates from the reference value when the ratio of the transcript ratio and the reference value exceeds or falls below a cutoff. In some embodiments, the transcript ratio deviates from the reference value when the difference between the transcript ratio and the reference value exceeds a cutoff.

The method generally identifies a gene as associated with a pregnancy-associated disorder if the expression level of that gene differs significantly in pregnancies that do and do not demonstrate the disorder, all else being equal.

The diagnosis and monitoring of fetal disorders and pregnancy pathologies has previously been achieved by using maternal plasma RNAs that are associated with diseases. For example, the maternal plasma level of corticotrophin releasing hormone (CRH) mRNA has been shown to be useful for the noninvasive detection and prediction of preeclampsia[2,3]. The detection of interleukin 1 receptor-like 1 (IL1RL1) mRNA in maternal plasma has been demonstrated to be useful for identifying women with spontaneous preterm birth[8]. A panel of growth-related maternal plasma RNA markers had also been investigated for the noninvasive assessment of fetal growth and intrauterine growth restriction[4]. In this study, we reason that novel disease-associated circulating RNA markers could be identified by directly compared the maternal plasma transcriptomes of normal pregnant women and women with complicated pregnancies, such as preeclampsia, intrauterine growth restriction, preterm labour and fetal aneuploidies. To demonstrate the feasibility of this approach, we performed RNA-Seq for maternal plasma samples obtained from three pregnant women who developed preeclampsia and seven uncomplicated pregnant women of matched gestations. We identified 98 transcripts that showed significant elevation in the plasma of preeclamptic pregnant women (FIG. 26). The newly identified preeclampsia-associated transcripts are potentially useful for prediction, prognostication and monitoring of the disease.

This technology can also be used for the prediction and monitoring of preterm labour. The technology can also be used for the prediction of imminent fetal demise. The technology can also be used for detecting diseases caused by gene mutations, as long as the gene concerned is transcribed in fetal or placental tissues and the transcripts are detectable in maternal plasma.

Plasma RNA-Seq can be applied in other clinical scenarios. For example, the plasma RNA-Seq methodology developed in this study would be potentially useful for studying other pathological conditions, such as cancer, in which aberrant plasma RNA concentrations have been reported[13,14]. For example, by comparing the plasma transcriptomes of a cancer patient before and after therapy, tumor-associated circulating RNA markers may be identified for noninvasive diagnostic application.

VI. Allelic Expression Patterns of Specific Genes

RNA-sequencing has been employed to examine the allelic expression pattern[25]. We postulated that the allelic expression pattern for a given gene would be retained when the RNA transcripts were released from the tissues into the circulation, hence could be detected in the plasma. In this study, we have examined the allelic counts of two RNA transcripts, namely PAPPA, a pregnancy-specific gene, and H19, an imprinted maternally expressed gene[26,27].

For the PAPPA gene, we analyzed a SNP, rs386088, which contains a fetal-specific SNP allele (FIG. 27). The absence of PAPPA RNA-seq reads in the post-delivery plasma samples indicated that it was indeed pregnancy-specific[4]. Of note, there was no statistically significant difference in the proportions of fetal-allele read counts between the pre-delivery maternal plasma and the placental RNA samples (P=0.320, $\chi^2$ test), indicating that the maternal plasma data reflected the bi-allelic expression pattern of PAPPA in the placenta.

Figure 29:
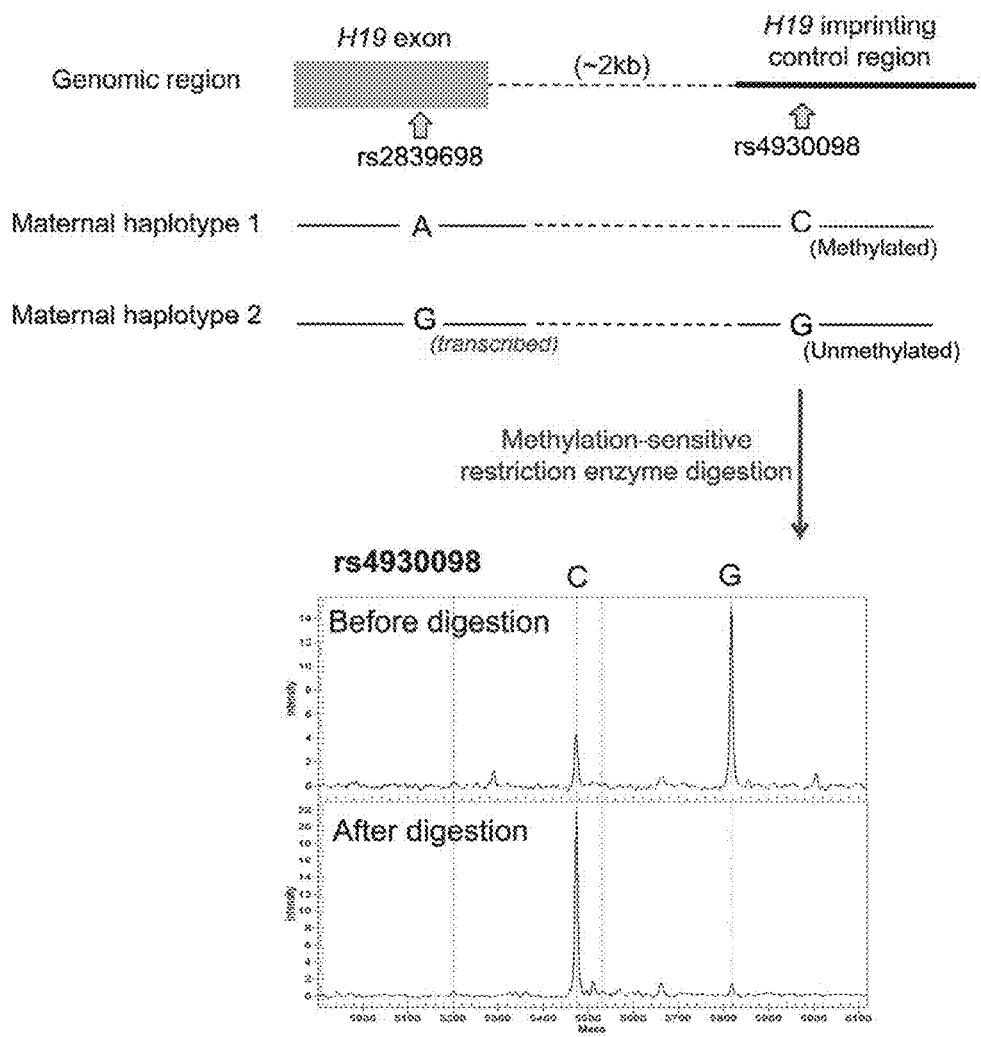
FIG. 29 shows detection of maternal H19 methylation status by methylation-sensitive restriction enzyme digestion.

We have recently reported that the DNA methylation pattern of the imprinted maternally expressed H19 gene in the placenta and the maternal blood cells could be detected by bisulfite DNA sequencing of maternal plasma DNA[28]. Here, we have further examined whether the genomic imprinting status of H19 gene could be explored at the RNA level. We first focused on a SNP site in exon 1 of the H19 gene, rs2839698, which contains a maternal-specific allele, i.e. AA in the fetus and AG in the mother. As shown in FIG. 28, only G-allele was detected in the post-delivery plasma (FIG. 28). Such monoallelic pattern was in accordance with its linkage to the unmethylated G-allele on the rs4930098 SNP site in the imprinting control region (FIG. 29). In the pre-delivery maternal plasma, while G-allele was present, A-allele, which was contributed by the placenta, was also detected (FIG. 28). In three other SNP sites, i.e. rs2839701, rs2839702 and rs3741219, which bear maternal-specific alleles, a similar allelic pattern was found, i.e. bi-allelic in the pre-delivery maternal plasma and monoal-lelic in the post-delivery maternal plasma (FIG. 28). It might be that the maternal-specific alleles on these SNP sites were in the same maternal haplotype, which was unmethylated and therefore being transcribed. Notably, H19 RNA was not expressed in the maternal blood cells (FIG. 28), suggesting that the H19 RNA molecules in the plasma were derived from maternal tissues/organs other than the blood cells. Non-placental and non-fetal tissues that have been reported to show H19 expression included the adrenal gland, skeletal muscles, uterus, adipocytes, liver and pancreas[29].

VII. Discussion

In this work, we aimed to develop a technology for providing a global view of the transcriptomic activities in maternal plasma using RNA-seq. We have previously shown that the fractional fetal DNA in maternal plasma can be calculated by targeting one or several fetal-specific loci because the whole fetal genome is evenly represented in the maternal plasma[30]. Unlike circulating DNA, measurement of the proportion of fetal-derived RNA transcripts in the maternal plasma is less straightforward as it is complicated by differential gene expression in the fetal and maternal tissues and perhaps their release into the circulation. By performing RNA-seq on maternal plasma and examining the polymorphic differences between the fetus and the mother, we were able to estimate the proportion of plasma transcripts contributed by the fetus. While maternal-derived transcripts dominated the plasma transcriptome, as one would anticipate, 3.70% and 11.28% of the circulating transcripts in the maternal plasma were derived from the fetus during early and late pregnancy, respectively. These fetal-derived transcripts include the RNA molecules co-contributed by the fetus and the mother, as well as those contributed solely by the fetus. We found the latter to constitute 0.90% and 2.52% of the maternal circulating transcripts, during early and late pregnancy, respectively. The higher representation of such fetal-specific genes during late pregnancy is perhaps correlated with an increase in the size of the fetus and the placenta as pregnancy progresses.

In this study, we have demonstrated that a balanced RNA allelic expression of the pregnancy-specific PAPPA gene in the placenta and the monoallelic expression of the imprinted maternally expressed H19 gene could be observed in the maternal plasma. These data suggest that the maternal plasma could be used as a noninvasive sample source for the study of allele expression patterns.

By quantitative comparison of the RNA transcripts in the pre- and post-delivery maternal plasma samples, we have compiled a list of 131 genes that were up-regulated during pregnancy, as evident by their reduced representation in the post-partum plasma samples. As expected, the profile of these genes could be used to differentiate plasma samples of pregnant women from those of the non-pregnant women. Such direct comparison of the pre- and post-delivery maternal plasma samples has allowed us to, in a high-throughput manner, sort out pregnancy-associated genes, which may not necessarily be expressed at a much higher level in the placenta than in the maternal blood cells as demonstrated in previous work[10,15]. In essence, this direct plasma examination method presents another avenue for the discovery of circulating pregnancy-associated RNA transcripts, without an a priori knowledge of the transcriptomic profiles of the placental tissues and the blood cells.

While we have shown that RNA-seq is a feasible method to profile the plasma transcriptome, several technical issues can be further improved. First, the information yield for plasma RNA-seq could be increased by further optimization of the sequencing protocol, particularly in depletion of the highly transcribed rRNA and globin genes from the plasma. Second, we have focused only on the reference transcripts and have not yet explored individual isoforms. Future studies could include detection of novel transcripts and differential analysis of the splicing variants and their isoforms[31-33] by increasing the sequencing read depth. Third, we have omitted ASE-filtering in the analysis of proportions of fetal- and maternal-derived transcripts for the early pregnancy samples as the chorionic villi and amniotic fluid had been exhausted for the genotyping analysis. Nonetheless, we have shown in late pregnancy that ASE-filtering had no pronounced impact on the identification of genes with predominant fetal and maternal contributions in the maternal plasma (FIGS. 16 and 17).

In conclusion, we have demonstrated that RNA-seq technology can be used to measure the proportion of fetal-derived transcripts and to identify circulating pregnancy-associated genes in the maternal plasma. This study has paved the path towards better comprehension of the transcriptomic landscape of maternal plasma hence facilitating the identification of biomarker candidates involved in pregnancy-related diseases. We envision that this technology would lead to new avenues for molecular diagnostics for pregnancy- or placenta-related diseases, and also for other diseases such as cancer[34].

VIII. Transplantation

As mentioned above, methods described herein can also be applied to transplantation. The methods for transplantation can be proceed in a similar manner as for the fetal analysis. For example, a genotype of the transplanted tissue can be obtained. Embodiments can identify loci where the transplanted tissue is heterozygous, and where the host organism (e.g., male or female) is homozygous. And, embodiments can identify loci where the transplanted tissue is homozygous, and where the host organism (e.g., male or female) is heterozygous. The same ratios can be computed, and compared to a cutoff value to determine whether a disorder exists.

IX. Computer Systems

Figure 30:
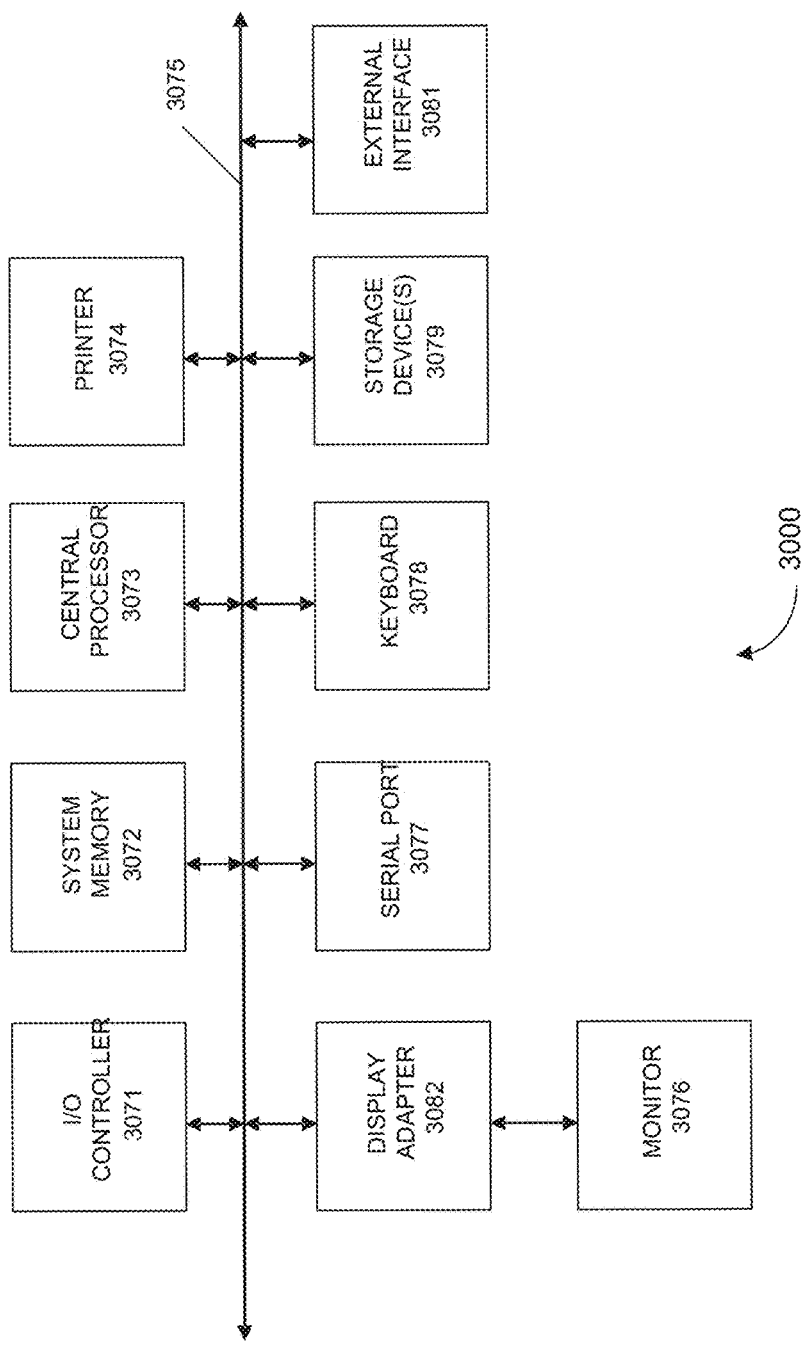
FIG. 30 shows a block diagram of an example computer system 3000 usable with system and methods according to embodiments of the present invention.

Any of the computer systems mentioned herein may utilize any suitable number of subsystems. Examples of such subsystems are shown in FIG. 30 in computer apparatus 3000. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 30 are interconnected via a system bus 3075. Additional subsystems such as a printer 3074, keyboard 3078, storage device(s) 3079, monitor 3076, which is coupled to display adapter 3082, and others are shown. Peripherals and input/output (I/O) devices, which couple to I/O controller 3071, can be connected to the computer system by any number of means known in the art, such as serial port 3077. For example, serial port 3077 or external interface 3081 (e.g. Ethernet, Wi-Fi, etc.) can be used to connect computer system 3000 to a wide area network such as the Internet, a mouse input device, or a scanner. The interconnection via system bus 3075 allows the central processor 3073 to communicate with each subsystem and to control the execution of instructions from system memory 3072 or the storage device(s) 3079 (e.g., a fixed disk, such as a hard drive or optical disk), as well as the exchange of information between subsystems. The system memory 3072 and/or the storage device(s) 3079 may embody a computer readable medium. Any of the data mentioned herein can be output from one component to another component and can be output to the user.

A computer system can include a plurality of the same components or subsystems, e.g., connected together by external interface 3081 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

X. REFERENCES

1. Ng E K O, Tsui N B Y, Lau T K, Leung T N, Chiu R W K, Panesar N S, Lit L C, Chan K W, Lo Y M D. mRNA 1. of placental origin is readily detectable in maternal plasma. Proc Natl Acad Sci USA 2003; 100: 4748-53.
2. Ng E K O, Leung T N, Tsui N B Y, Lau T K, Panesar N S, Chiu R W K, Lo Y M D. The concentration of circulating corticotropin-releasing hormone mRNA in maternal plasma is increased in preeclampsia. Clin Chem 2003; 49: 727-31.
3. Farina A, Sekizawa A, Sugito Y, Iwasaki M, Jimbo M, Saito H, Okai T. Fetal DNA in maternal plasma as a screening variable for preeclampsia. A preliminary non-parametric analysis of detection rate in low-risk nonsymptomatic patients. Prenat Diagn 2004; 24: 83-6.
4. Pang W W, Tsui M H, Sahota D, Leung T Y, Lau T K, Lo Y M, Chiu R W. A strategy for identifying circulating placental RNA markers for fetal growth assessment. Prenat Diagn 2009; 29: 495-504.
5. Lo Y M D, Tsui N B Y, Chiu R W K, Lau T K, Leung T N, Heung M M, Gerovassili A, Jin Y, Nicolaides K H, Cantor C R, Ding C. Plasma placental RNA allelic ratio permits noninvasive prenatal chromosomal aneuploidy detection. Nat Med 2007; 13: 218-23.
6. Tsui N B Y, Akolekar R, Chiu R W K, Chow K C K, Leung T Y, Lau T K, Nicolaides K H, Lo Y M D. Synergy of total PLAC4 RNA concentration and measurement of the RNA single-nucleotide polymorphism allelic ratio for the noninvasive prenatal detection of trisomy 21. Clin Chem 2010; 56: 73-81.
7. Tsui N B Y, Wong B C K, Leung T Y, Lau T K, Chiu R W K, Lo Y M D. Non-invasive prenatal detection of fetal trisomy 18 by RNA-SNP allelic ratio analysis using maternal plasma SERPINB2 mRNA: a feasibility study. Prenat Diagn 2009; 29: 1031-7.
8. Chim S S, Lee W S, Ting Y H, Chan O K, Lee S W, Leung T Y. Systematic identification of spontaneous preterm birth-associated RNA transcripts in maternal plasma. PLoS One 2012; 7: e34328.
9. Wong B C K, Chiu R W K, Tsui N B Y, Chan K C A, Chan L W, Lau T K, Leung T N, Lo Y M D. Circulating placental RNA in maternal plasma is associated with a preponderance of 5' mRNA fragments: implications for noninvasive prenatal diagnosis and monitoring. Clin Chem 2005; 51: 1786-95.
10. Tsui N B Y, Chim S S C, Chiu R W K, Lau T K, Ng E K O, Leung T N, Tong Y K, Chan K C A, Lo Y M D. Systematic micro-array based identification of placental mRNA in maternal plasma: towards non-invasive prenatal gene expression profiling. J Med Genet 2004; 41: 461-7.
11. Poon L L, Leung T N, Lau T K, Lo Y M D. Presence of fetal RNA in maternal plasma. Clin Chem 2000; 46:1832-4.
12. Go A T, Visser A, Mulders M A, Blankenstein M A, Van Vugt J M, Oudejans C B. Detection of placental transcription factor mRNA in maternal plasma. Clin Chem 2004; 50:1413-4.
13. Smets E M, Visser A, Go A T, van Vugt J M, Oudejans C B. Novel biomarkers in preeclampsia. Clin Chim Acta 2006; 364:22-32.
14. Purwosunu Y, Sekizawa A, Koide K, Farina A, Wibowo N, Wiknjosastro G H, et al. Cell-free mRNA concentrations of plasminogen activator inhibitor-1 and tissue-type plasminogen activator are increased in the plasma of pregnant women with preeclampsia. Clin Chem 2007; 53:399-404.
15. Miura K, Miura S, Yamasaki K, Shimada T, Kinoshita A, Niikawa N, et al. The possibility of microarray-based analysis using cell-free placental mRNA in maternal plasma. Prenat Diagn 2010; 30:849-61.
16. Ng E K O, El-Sheikhah A, Chiu R W K, Chan K C, Hogg M, Bindra R, et al. Evaluation of human chorionic gonadotropin beta-subunit mRNA concentrations in maternal serum in aneuploid pregnancies: a feasibility study. Clin Chem 2004; 50:1055-7.
17. Mortazavi A, Williams B A, McCue K, Schaeffer L, Wold B. Mapping and quantifying mammalian transcriptomes by RNA-Seq. Nat Methods 2008; 5:621-8.
18. Sultan M, Schulz M H, Richard H, Magen A, Klingenhoff A, Scherf M, et al. A global view of gene activity and alternative splicing by deep sequencing of the human transcriptome. Science 2008; 321:956-60.
19. Kim J, Zhao K, Jiang P, Lu Z X, Wang J, Murray J C, Xing Y. Transcriptome landscape of the human placenta. B M C Genomics 2012; 13:115.
20. Wang K, Li H, Yuan Y, Etheridge A, Zhou Y, Huang D, et al. The complex exogenous RNA spectra in human plasma: an interface with human gut biota? PLoS One 2012; 7:e51009.
21. Li H, Guo L, Wu Q, Lu J, Ge Q, Lu Z. A comprehensive survey of maternal plasma miRNAs expression profiles using high-throughput sequencing. Clin Chim Acta 2012; 413:568-76.
22. Williams Z, Ben-Dov I Z, Elias R, Mihailovic A, Brown M, Rosenwaks Z, Tuschl T. Comprehensive profiling of circulating microRNA via small RNA sequencing of cDNA libraries reveals biomarker potential and limitations. Proc Natl Acad Sci USA 2013; 110:4255-60.
23. Chim S S C, Shing T K, Hung E C, Leung T Y, Lau T K, Chiu R W K, Lo Y M D. Detection and characterization of placental microRNAs in maternal plasma. Clin Chem 2008; 54:482-90.
24. Pickrell J K et al. Understanding mechanisms underlying human gene expression variation with RNA sequencing. Nature 2010; 464:768-772.
25. Smith R M, Webb A, Papp A C, Newman L C, Handelman S K, Suhy A, et al. Whole transcriptome RNA-Seq allelic expression in human brain. B M C Genomics 2013; 14:571.
26. Frost J M, Monk D, Stojilkovic-Mikic T, Woodfine K, Chitty L S, Murrell A, et al. Evaluation of allelic expression of imprinted genes in adult human blood. PLoS One 2010; 5:e13556.
27. Daelemans C, Ritchie M E, Smits G, Abu-Amero S, Sudbery I M, Forrest M S, et al. High-throughput analysis of candidate imprinted genes and allele-specific gene expression in the human term placenta. B M C Genet 2010; 11:25.
28. Lun F M F, Chiu R W K, Sun K, Leung T Y, Jiang P, Chan K C A, et al. Noninvasive prenatal methylomic analysis by genomewide bisulfite sequencing of maternal plasma DNA. Clin Chem 2013; 59:1583-94.
29. Wu C, Orozco C, Boyer J, Leglise M, Goodale J, Batalov S, et al. BioGPS: an extensible and customizable portal for querying and organizing gene annotation resources. Genome Biol 2009; 10:R130.
30. Lo Y M D, Chan K C A, Sun H, Chen E Z, Jiang P, Lun F M F, et al. Maternal plasma DNA sequencing reveals the genome-wide genetic and mutational profile of the fetus. Sci Transl Med 2010; 2:61ra91.
31. Cabili M N, Trapnell C, Goff L, Koziol M, Tazon-Vega B, Regev A, Rinn J L. Integrative annotation of human large intergenic noncoding RNAs reveals global properties and specific subclasses. Genes Dev 2011; 25:1915-27.

32. St Laurent G, Shtokalo D, Tackett M R, Yang Z, Eremina T, Wahlestedt C, et al. Intronic RNAs constitute the major fraction of the non-coding RNA in mammalian cells. B M C Genomics 2012; 13:504.
33. Anders S, Reyes A, Huber W. Detecting differential usage of exons from RNA-seq data. Genome Res 2012; 22:2008-17.
34. Fleischhacker M, Schmidt B. Circulating nucleic acids (CNAs) and cancer—a survey. Biochim Biophys Acta 2007; 1775:181-232.

What is claimed is:

1. A method of diagnosing a pregnancy-associated disorder using a sample from a female subject pregnant with a fetus, the method comprising:
    applying an assay to RNA molecules obtained from the sample to generate a plurality of reads that include different alleles at one or more loci for measuring relative expression levels between the different alleles in the sample, wherein the assay does not target a reference gene for normalizing expression levels;
    receiving the plurality of reads, wherein the reads are obtained from an analysis of RNA molecules obtained from the sample, the sample containing a mixture of maternal- and fetal-derived RNA molecules;
    identifying, by a computer system, locations of the reads in a reference sequence;
    identifying one or more informative loci, each of which is homozygous in a first entity for a corresponding first allele and which is heterozygous in a second entity for the corresponding first allele and a corresponding second allele, wherein the first entity is the pregnant female subject or the fetus, and the second entity is the other one of the pregnant female subject and the fetus;
    filtering the one or more informative loci to identify one or more filtered informative loci:
        that are located within an expressed region of the reference sequence,
        at which at least a first predetermined number of reads in the plurality of reads containing the corresponding first allele are located, and
        at which at least a second predetermined number of reads in the plurality of reads containing the corresponding second allele are located,
    for each of the one or more filtered informative loci:
        determining a first number of reads located at the filtered informative locus and containing the corresponding first allele, and
        determining a second number of reads located at the filtered informative locus and containing the corresponding second allele,
    calculating a first sum of the first numbers and the second sum of the second numbers;
    calculating a ratio of the first sum and the second sum, and comparing the ratio to a cutoff value to determine whether the fetus, mother, or pregnancy has a pregnancy-associated disorder, the cutoff value being determined from one or more samples obtained from pregnant female subjects without the pregnancy-associated disorder, thereby determining whether the fetus, mother, or pregnancy has a pregnancy-associated disorder without normalizing with respect to a reference gene or a total amount of RNA molecules in the sample.

2. The method of claim 1, wherein the sample of the pregnant woman is a sample of blood plasma.

3. The method of claim 1, wherein the second entity is the pregnant female subject.

4. The method of claim 1, wherein the second entity is the fetus.

5. The method of claim 1, wherein calculating a ratio of the first sum and the second sum comprises dividing the second sum by a sum of the first sum and the second sum.

6. The method of claim 1, wherein the analysis of RNA molecules obtained from the sample comprises sequencing the RNA molecules or cDNA copies thereof.

7. The method of claim 1, wherein the analysis of RNA molecules obtained from the sample comprises performing digital PCR.

8. The method of claim 1, wherein identifying locations of the reads in a reference sequence comprises aligning the reads to the reference sequence.

9. The method of claim 1, wherein the first predetermined number of reads is 1, and wherein the second predetermined number of reads is 1.

10. The method of claim 1, further comprising sequencing genomic DNA obtained from maternal tissue to determine a genotype of the pregnant female subject at each informative locus.

11. The method of claim 1, further comprising sequencing genomic DNA obtained from the placenta, chorionic villi, amniotic fluid, or maternal plasma to determine a genotype of the fetus at each informative locus.

12. The method of claim 1, further comprising estimating a portion of RNA in the sample that is of maternal or fetal origin, wherein the portion is the ratio multiplied by a scalar representing a total expression level at the filtered informative loci relative to expression of the second alleles in the second entity.

13. A computer product comprising a computer readable medium storing a plurality of instructions for controlling a processor to perform an operation of the method of claim 1.

14. The method of claim 1, further comprising:
    performing a random sequencing of RNA molecules obtained from the sample to obtain the plurality of reads,
    wherein identifying locations of the reads in the reference sequence comprises aligning the reads to a transcriptome.

15. The method of claim 1, wherein the plurality of reads includes at least 3 million reads.

16. The method of claim 1, further comprising:
    obtaining a blood sample from the female subject, and
    extracting plasma from the blood sample to obtain the biological sample.

17. The method of claim 1, wherein the pregnancy-associated disorder is selected from the group consisting of preeclampsia, intrauterine growth restriction, invasive placentation, pre-term birth, hemolytic disease of the fetus, placental insufficiency, hydrops fetalis, fetal malformation, HELLP syndrome, systemic lupus erythematosus, and an immunological disease of the female subject pregnant with the fetus.

18. The method of claim 1, further comprising displaying the determination of whether the fetus, mother, or pregnancy has a pregnancy-associated disorder.

19. The method of claim 1, further comprising:
    determining the fetus, mother, or pregnancy has a pregnancy-associated disorder, and
    treating the fetus, mother, or pregnancy for the pregnancy-associated disorder.

20. The method of claim 1, wherein the method does not use prior genotyping information of a placenta.

* * * * *